(12) United States Patent
Dahl et al.

(10) Patent No.: US 6,635,278 B1
(45) Date of Patent: Oct. 21, 2003

(54) PHARMACEUTICAL FORMULATIONS

(75) Inventors: Terrence C. Dahl, Sunnyvale, CA (US); Lung-Chi J. Yuan, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 09/211,613

(22) Filed: Dec. 15, 1998

(51) Int. Cl.$^7$ .............................. A61K 9/20; A61K 9/14; A61K 9/48

(52) U.S. Cl. ........................ 424/465; 424/451; 424/452; 424/464; 424/489

(58) Field of Search ................................ 424/464, 465, 424/451, 457, 489, 452

(56) References Cited

U.S. PATENT DOCUMENTS

| | | | |
|---|---|---|---|
| 5,562,921 A | 10/1996 | Sherman | 424/465 |
| 5,663,159 A | 9/1997 | Starrett, Jr. et al. | 514/181 |
| 5,919,776 A | * 7/1999 | Hagmann et al. | 514/159 |
| 6,268,354 B1 | * 7/2001 | Nishimura et al. | 514/110 |

FOREIGN PATENT DOCUMENTS

| | | | |
|---|---|---|---|
| EP | 0.205.826 | | 12/1986 |
| EP | 0 213 761 A2 | | 3/1987 |
| WO | WO 94/22435 | | 10/1994 |
| WO | WO 99/04774 | * | 2/1999 |

OTHER PUBLICATIONS

Badawy et al., "Chemical Stability of an Ester Prodrug of a Glycoprotein IIb/IIIa Receptor Antagonist in Solid Dosage Forms", 88(4):428–433, J Pharm Sci, Apr. 1999.

Brandl et al., "Approaches for Improving the Stability of Ketorolac in Powder Blends", 84(10):1151–1153, J Pharm Sci, Oct. 1995.

Gu et al., "Drug–Excipient Incompatibility Studies of the Dipeptide Angiotensin–Converting Enzyme Inhibitor, Moexipril Hydrochloride: Dry Powder vs Wet Granulation", 7(4):379–383, Pharm Res, 1990.

Kalatzis, "Reactions of Acetaminophen in Pharmaceutical Dosage Forms: Its Proposed Acetylation by Acetylsalicyclic Acid", 59(2):193–196, J Pharm Sci, Feb. 1970.

Kornblum et al., "Pharmaceutical Heterogeneous Systems I", 56(12):1569–1575, J Pharm Sci, Dec. 1967.

Koshy, et al., "Acetylation of Acetaminophen in Tablet Formulations Containing Aspirin", 56(9): 1117–1121, J. Pharm Sci, Sep. 1967.

Lee et al., "Simulation of the temporal water activity profile in induction–sealed HDPE containers desiccated with silica gel", Poster, AAPS, Apr. 24 & 25, 1997.

Lee et al., "Characterization of the Thermal Decomposition of Adefovir Dipivoxil in the Solid State", Poster, AAPS, Apr. 24 & 25, 1997.

Sayer et al., "Mechanism of Carbinolamine Formation", 96(26): 7998–8009, J Am Chem Soc, Dec. 25, 1974.

Troup et al., "Degradation of Phenylephrine Hydrochloride in Tablet Formulations Containing Aspirin", 53(4):375–379, J Pharm Sci, Apr. 1964.

Zoglio et al., "Pharmaceutical Heterogeneous Systems III", 57(11): 1877–1880, J Pharm Sci, Nov. 1968.

Krise et al, "Prodrugs of phosphates, phosphonates, and phosphinates", 19:287–310, Advanced Drug Delivery Reviews, May 22, 1996.

* cited by examiner

Primary Examiner—Thurman K. Page
Assistant Examiner—S. Tran
(74) Attorney, Agent, or Firm—Max D. Hensley

(57) ABSTRACT

The invention provides compositions comprising the nucleotide analog 9-[2-[[bis[(pivaloyloxy)methyl]phosphono]methoxy]ethyl]adenine and an alkaline excipient with or without L-carnitine-L-tartrate. The compositions are more stable those previously described. The invention also provides methods to make the compositions and their intermediates.

26 Claims, No Drawings

PHARMACEUTICAL FORMULATIONS

BACKGROUND OF THE INVENTION

The invention relates to pharmaceutical formulations for human or veterinary use that contain the nucleotide analog 9-[2-[[bis[(pivaloyloxy)methyl]phosphono]methoxy]ethyl] adenine (adefovir dipivoxil or hereafter "AD"). The present invention also relates to methods to prepare the formulations.

AD is the bis-pivaloyloxymethyl ester of the parent compound 9-[2-(phosphonomethoxy)ethyl]adenine ("PMEA"), which has antiviral activity in animals and in humans. AD and PMEA have been described, e.g., U.S. Pat. Nos. 4,724,233 and 4,808,716, EP 481 214, Benzaria et al., "Nucleosides and Nucleotides" 14(3–5):563–565, 1995, Holy et al., "Collect. Czech. Chem. Commun." 54:2190–2201, 1989, Holy et al., "Collect. Czech. Chem. Commun." 52:2801–2809, 1987, Rosenberg et al., "Collect. Czech. Chem. Commun." 53:2753–2777, 1988, Starrett et al., "Antiviral Res." 19:267–273, 1992 and Starrett et al., "J. Med. Chem." 37:1857–1864, 1994. Heating of solid AD resulted in a decomposition process initiated by hydrolysis (Lee et al., Amer. Assoc. Pharm. Sci., Western Regional Meeting, poster Nos. F-1 and F-2, Apr. 24–25, 1997).

Prior AD formulations have not contained alkaline excipients. Typical AD formulations contain pregelatinized starch, croscarmellose sodium, lactose monohydrate, talc and magnesium stearate. Such compositions are typically packaged with up to 5 g of silica gel as a desiccant. The desiccant is needed to allow storage of AD of at least 2 years at room temperature.

OBJECTS OF THE INVENTION

The invention compositions or methods accomplish one or more of the following objects.

A principal object of the invention is to provide AD formulations having improved stability, whereby the amount or presence of stabilizing means such as silica gel or activated carbon is reduced or eliminated and the formulations can be stored at room temperature.

Another object is to provide compositions used as intermediates to prepare the AD formulations.

Other objects are to provide methods to make the AD formulations.

SUMMARY OF THE INVENTION

In accordance with the objects, the invention provides formulations comprising AD and an alkaline excipient with or without L-carnitine-L-tartrate.

Embodiments include intermediate compositions containing AD and AD formulations in the form of unit dosages, such as tablets or capsules typically comprising about 2–50% AD and about 0.001–10% alkaline excipient.

Other embodiments include a product produced by the process of contacting a mixture comprising AD and an alkaline excipient.

Other embodiments include a method comprising mixing AD with an alkaline excipient to obtain a mixture.

Other embodiments include methods to make a formulation comprising AD and an alkaline excipient by wet granulation or by direct compression.

Other embodiments include a product made by the process of preparing a formulation comprising AD and an alkaline excipient by wet granulation or by direct compression.

DETAILED DESCRIPTION OF THE INVENTION

Formulations such as tablets comprising AD and an alkaline excipient were found to have a significantly improved stability when stored at room temperature (about 15–25° C. as used herein) in closed containers compared to control formulations lacking an alkaline excipient. Without being bound to any theory, it appears that the alkaline excipient stabilizes AD by adjusting the local pH or by reducing the rate of AD degradation product formation. The pivaloyloxymethyl moieties in AD, esters of PMEA, are typically susceptible to acid- and base-catalyzed hydrolysis. Aqueous AD solutions have their maximum stability at a low pH, about 3–5, but AD tablets containing acidic excipients, such as citric acid, actually compromised the stability of AD compared to control formulations lacking acidic excipients. Thus the stabilizing effect of alkaline excipients on AD was not reasonably predictable.

The invention formulations permit storage at room temperature with a reduced or eliminated requirement for packaging aids such as silica gel or activated carbon. The formulations also allow the use of AD preparations that are about 97% pure AD while retaining sufficient stability to retain a shelf-life of at least 2 years at room temperature. As used here, "shelf-life" means the storage time at room temperature that one can hold a formulation while the purity of the AD remains at ≧ about 92% purity.

AD is a nucleotide analog having antiviral activity against HIV, HBV, CMV, and several other viruses. It has the following structure.

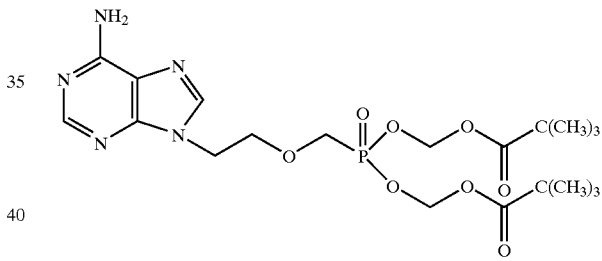

Anhydrous crystalline AD is preferred in invention compositions over previously described amorphous AD, see, Starrett et al., "J. Med. Chem." 19:1857–1864, 1994. U.S. application 08/900,745 describes crystalline forms of AD.

When one prepares invention compositions using anhydrous crystalline AD, a portion of the AD may comprise the crystalline dihydrate of AD (AD.2H$_2$O) or amorphous AD. The portion of the crystalline dihydrate of AD or amorphous AD will typically be less than about 20% of the AD that is present. These forms may arise during processing of intermediate compositions and formulations. For example, some invention compositions comprising L-carnitine-L-tartrate may generate some AD.tartrate during processing or storage. AD used in invention compositions may comprise other crystalline salts such as AD.½H$_2$SO$_4$, AD.HBr, AD.HCl, AD.HNO$_3$, AD.CH$_3$SO$_3$H, AD.C$_2$H$_5$SO$_3$H, AD.β-naphthalene sulfonic acid, AD.α-naphthalene sulfonic acid, AD.(S)-camphor sulfonic acid, AD.fumaric acid, AD.succinic acid, AD.maleic acid, AD.ascorbic acid or AD.nicotinic acid.

Anhydrous AD crystals generally have a median size by light scattering of about 25–150 μm, usually about 30–80 μm. Individual anhydrous AD crystal preparations usually comprise crystals that have a length range of about 1–200

μm and have a typical maximum dimension for individual crystals in a preparation of about 60–200 μm. In some preparations, about 1–10% of the crystals will have a maximum dimension of greater than 250 μm. Anhydrous AD crystals typically have tablet, plate, needle, and/or irregular habits. Aggregates of anhydrous crystals also occur with a typical diameter range of about 25–150 μm. Anhydrous AD crystals are usually used to prepare invention compositions. However, during wet granulation and other processing steps needed to prepare formulations, a portion of the crystals may convert to an amorphous form or absorb water to form AD.2H$_2$O crystals. Anhydrous AD crystals have an endothermic transition as measured by differential scanning calorimetry at about 102° C. (usually 102±1° C.).

AD.2H$_2$O crystals typically have a median size of about 15–85 μm by light scattering, ordinarily about 25–80 μm. Individual AD.2H$_2$O crystal preparations usually contain crystals that have a length range of about 1–300 μm. Anhydrous AD crystals have an endothermic transition as measured by differential scanning calorimetry at about 73° C. (usually 73±1° C.).

As used herein "excipient" means a component or an ingredient that is acceptable in the sense of being compatible with the other components of the formulation and not deleterious to a patient or animal to which the formulation is to be administered.

"Alkaline excipient," as used herein, is an excipient with a pK$_a$ of the conjugated acid of at least about 4.0 and that has a K$_{sp}$ of about $1\times10^{-3}$ to about $1\times10^{-15}$, usually about $1\times10^{-4}$ to about $1\times10^{-11}$. Alkaline excipients are usually an alkaline carbonate or an alkaline hydroxide. Alkaline carbonates include calcium carbonate, magnesium carbonate, zinc carbonate, manganese carbonate, aluminum carbonate, ferrous carbonate or cobalt carbonate. Alkaline hydroxides include magnesium hydroxide, calcium hydroxide, aluminum hydroxide or iron hydroxide.

As used herein and unless otherwise stated or implied by context, the terms "excipient" or "alkaline excipient" or a specific type of excipient, means one or more excipients, alkaline excipients or excipient types may be present. For example, "lubricant", or "binder" means one, two or more lubricants or binders together constitute the indicated component in the specified amount (if any). Usually, only one or two excipients of a given type are present in a given invention composition.

As used herein and unless otherwise stated or implied by context, expressions of a percentage of a component mean percent of the component by weight (w/w). Thus, 20% AD means 20% w/w AD is present in an intermediate composition or a formulation. The amount of excipient indicated in invention compositions is not affected by the form of component or excipient used, i.e., anhydrous or hydrated. Thus, an invention composition that contains about 50% lactose can instead contain about 50% lactose monohydrate.

As used herein, the amount of solvent used in wet granulation methods is expressed as a percentage of the weight of dry intragranular components. Thus, if 10 kg of dry intragranular components are present, 10% water used for wet granulation means 1 kg of water. In formulations, the amount of solvent remaining after drying is expressed as a percentage of the weight of all components, e.g., 1.5% solvent in an invention composition after drying means 1.5% of the total weight is solvent remaining after drying by a given method at a specified temperature.

Invention compositions include both formulations and intermediate compositions used to prepare formulations. As used herein, the term "formulation(s)" means any composition(s) containing AD, an alkaline excipient and optionally another excipient(s), that is intended for therapeutic use without further manufacturing. Formulations include finished dosage forms such as tablets, capsules or powders for preparing solutions or suspensions. Formulations are suitable for human or veterinary applications. "Intermediate composition(s)" means a composition that requires further processing before it is a formulation, e.g., mixing, wet granulation, drying, milling, compression into tablets, filling into capsules or packaging for sale or distribution.

The term, "wet granulation" means a process wherein liquid is contacted with AD and one or more excipients ("intragranular excipients") of an intermediate composition. These compositions are referred to as "intragranular compositions". The intragranular compositions are blended, mixed with a granulating solvent, dried and milled to obtain granules of a desired particle size or size range. The intragranular compositions are either directly compressed into a formulation, or are mixed or blended with additional components, usually excipients, which are referred to as extragranular excipients or components, followed by conversion into a dosage form, typically by compression. Usually, AD, an alkaline excipient and one or more additional excipients such as a diluent (lactose, lactose monohydrate, microcrystalline cellulose or L-carnitine-L-tartrate) are present as intragranular components. Invention embodiments include intragranular compositions that comprise AD and an alkaline excipient.

"Direct compression" means a process of physically mixing or blending AD and one or more excipients in an intermediate composition, followed by compressing and milling to obtain granules of a desired particle size or size range. The granules containing AD are either directly compressed into a formulation, or are mixed or blended with additional excipients, which are then converted into a dosage form, typically by compression.

Methods have been described, for example Karl Fischer (KF) or loss on drying (LOD), to determine liquid, e.g., water, content of solids, such as tablets, powders and granules. LOD measures all volatiles in a sample, while KF is typically used to measure all water. Thus, for a sample containing only water, LOD values are usually less than or equal to KF values for a given sample, e.g., LOD does not measure water in the crystal of the lactose monohydrate, but KF includes it. Granules containing AD, an alkaline excipient and other excipients are conveniently tested for water content by Karl Fischer titration using a Metrohm 684 KF Coulometer according to a published procedure (U.S. Pharmacopoeia, vol. 23, 1995, chapter <921>, U.S. Pharmacopeial Convention, Inc., Rockville, Md.) and manufacturer's Coulometer instructions. The amount of granules used in the assay, about 50–100 mg, is measured using a five place analytical balance (Sartorius, Model RC210D, or equivalent).

LOD was determined at 75° C. using a Mettler LP 16 infrared dryer (Hightstown, N.J.) equipped with a Mettler PM 400 balance and a Mettler GA45 printer. Approximately 2 g of granules, powder blends or ground materials from tablets were accurately weighed and then evenly spread on an aluminum sample pan (10 cm diameter, Mettler, Cat. No. 13865) and the LOD value determined by drying the sample at 75° C. for at least 15 minutes.

Embodiments include intermediate compositions that transiently occur when a method step or operation is performed. For example, when an alkaline excipient is brought into contact with AD, the composition before mixing or blending is a non-homogenous mixture. As the alkaline excipient is mixed or blended with the AD, the mixture's homogeneity increases. These transient compositions or intermediate compositions arise when a process step is performed and they are expressly included as invention embodiments whenever AD and an alkaline excipient are contacted or are present together.

Formulations of the present invention suitable for oral administration include discrete units such as sachets, cachets, capsules or tablets each containing a predetermined amount of AD; as a powder or granules. The formulations may also be presented as a bolus, electuary or paste.

Invention formulations or intermediate compositions generally comprise about 2–50% AD, usually about 10–30% and about 0.001–20% alkaline excipient, usually about 2–6%. In invention formulations where AD is present at a relatively low level, i.e., about 2–20%, alkaline excipient is typically present at about 1–6%. The invention formulations are usually presented as unit dosages suitable for oral administration once or twice per day, e.g., tablets or capsules. When intermediate compositions for compression into unit dosages contain less than about 15% AD, e.g., about 2–15%, they will typically contain about 10–40%, usually about 15–30%, of a suitable diluent, e.g., microcrystalline cellulose, to increase the compressed material's tensile strength, which is particularly useful to facilitate tablet coating processes. Unit dosages such as tablets or capsules will typically comprise about 1–300 mg of AD per unit, usually about 1–150 mg, e.g., about 5–60 mg for treatment of HBV or about 30–120 mg for treatment of HIV. Unit dosages will generally comprise about 10–30% AD and about 2–6% alkaline excipient.

In general, the alkaline excipient is an alkaline carbonate or an alkaline hydroxide. The formulations are typically characterized by having a solvent loss on drying at 75° C. of less than about 2.0%, usually less than about 1.5%. Intermediate compositions usually have a higher LOD until they are dried, e.g., an LOD of about 5% or more.

Some alkaline excipients are available in several chemical forms. For example, magnesium carbonate is commercially available in the forms shown below. When magnesium carbonate is present in the formulations, it may be present as any of these forms, but heavy magnesium carbonate and light magnesium carbonate, which are commercially available as United States Pharmacopoeia (U.S.P.) grade material, are preferred forms. The amount of alkaline excipient used in invention compositions is not affected by the form used, despite the presence of water.

| Description | Formula | % $MgCO_3$ | % $Mg(OH)_2$ |
|---|---|---|---|
| Magnesium carbonate anhydrous | $MgCO_3$ | 100 | 0 |
| Normal magnesium carbonate | $MgCO_3.xH_2O$ | — | 0 |
| Heavy magnesium carbonate | $3\ MgCO_3.Mg(OH)_2.4\ H_2O$ | 66.0 | 15.2 |
| Light magnesium carbonate | $3\ MgCO_3.Mg(OH)_2.3\ H_2O$ | 69.3 | 16.0 |
| Magnesium carbonate hydroxide | $4\ MgCO_3.Mg(OH)_2.5\ H_2O$ | 69.4 | 12.0 |

The alkaline excipient is preferably combined with AD in the form of as an intragranular excipient to maximize its physical contact with the AD drug substance in invention compositions. If used as an extragranular component, the alkaline excipient is present at higher levels, e.g., about 6–30%, usually about 15–25%.

Invention formulations usually include one or more other excipients such as a binder, disintegrant, diluent, lubricant, glidant, coloring agent or flavoring agent, see, e.g., U.S. Pat. Nos. 4,254,099; 4,517,179; 4,888,177; 5,427,800; 5,458,890. These excipients increase formulation stability, facilitate tablet compression during manufacture or accelerate disintegration after ingestion. Excipients are usually U.S.P., N.F. or U.S.P./N.F. grade, which are preferred grades for intermediate compositions and formulations. A given excipient, such as a binder may also have properties that overlap with the properties of other types of excipients. Thus, although we refer to lactose as a "diluent", lactose may also contribute to disintegration of a formulation.

A binder, such as hydroxypropylmethylcellulose, pregelatinized starch or povidone (polyvinylpyrrolidone), is typically present in invention compositions. Other binders may also be used, e.g., carboxymethylcellulose, methylcellulose, ethylcellulose or starch. The binder is used to enhance tablet tensile strength. The binder is typically present at a level of about 1–10%, often about 4–6%.

A disintegrant such as croscarmellose sodium, crospovidone or cross-linked cellulose is optionally present at a level of about 0.5–8%, usually at about 0.5–6%. The disintegrant facilitates tablet dissolution. It can be present in intragranular and extragranular portions, e.g., 2–3% in each, to facilitate uniform formulation or tablet dissolution.

A diluent such as microcrystalline cellulose, a carnitine salt, e.g., L-carnitine-L-tartrate or L-carnitine-fumarate, a monosaccharide or a disaccharide is optionally present at a level of about 20–80%, usually about 40–60%. Diluents include lactose, lactose monohydrate, sucrose and dextrose. The diluent is usually used to mask the physical properties of AD or to facilitate tablet dissolution. The diluent, microcrystalline cellulose, is available in several different forms, e.g., 50 and 100 µm nominal mean particle size, which are commercially available as Avicel™ (FMC Corp., Newark, Del.), as Emcocel™ (Edward Mendell Co. Inc., Carmel, N.J.) or Vivacel™ (J. Rettenmaier & Sohne GmbH). Microcrystalline cellulose in invention formulations is typically present as Avicel PH-102 or Avicel PH-112.

When L-carnitine-L-tartrate or L-carnitine-fumarate is present, the weight ratio in the formulation of AD:L-carnitine-L-tartrate or AD:L-carnitine-fumarate is about 1:4 to about 1:12 and typically the ratio is about 1:6. L-carnitine-L-tartrate is available commercially from Lonza Ltd. (Gampel, Switzerland) as a powder having a geometric mean particle size of about 400–600 µm. Particles milled to a geometric mean particle size of about 150–300 µm generally increases tablet strength and is preferred. When present, L-carnitine-L-tartrate or L-carnitine-fumarate is usually at a level of about 20–50%, usually about 40–50%. U.S. Pat. No. 5,073,376 describes L-carnitine-L-tartrate. L-Carnitine free base is hygroscopic and is not a preferred diluent but can be used in invention formulations. Carnitine salts that are non-hygroscopic are preferred in the formulations. The HCl salt of carnitine is also not preferred due to its hygroscopic character and its acidity, which destabilize AD.

The diagram below outlines different wet granulation processes for making AD intermediate compositions containing L-carnitine-L-tartrate: co-granulation, bi-granulation, and physical powder blend. AD is indicated in the diagram as GS-0840. These methods are also suitable for preparing intermediate compositions that do not contain L-carnitine-L-tartrate.

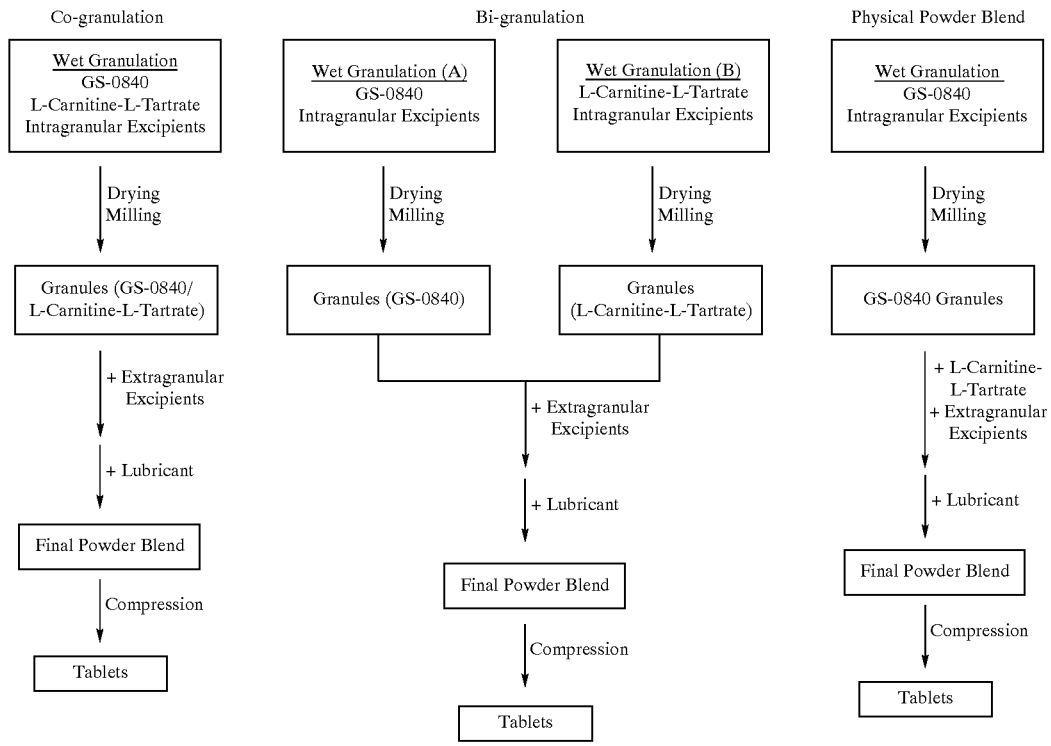

A lubricant such as magnesium stearate, talc or type I hydrogenated vegetable oil (Lubritab™, Mendell Co.; Sterotex™, Abitec) or sodium stearyl fumarate (Astra AB, Sweden) is typically present at a level of about 0.25–10%, usually about 0.5–7%, to facilitate tablet ejection during manufacture. Other lubricants may also be used in similar amounts, e.g., about 0.5–8% glyceryl behenate, glyceryl palmitostearate, sodium benzoate, calcium stearate or zinc stearate. For example, intermediate compositions or formulations may contain about 0.5–1% magnesium stearate and about 0–6% talc, or they may contain about 0.5–1% hydrogenated vegetable oil and about 2% talc, or about 0.5–3% sodium stearyl fumarate. Usually, the formulations contain one or two lubricants. When type I hydrogenated vegetable oil is present, it is usually at about 0.5–2%. Talc is usually also present with type I hydrogenated vegetable oil. Sodium stearyl fumarate has been described (Shah et al., "Drug Dev. Ind. Pharm." 12:1392–1346, 1986; Holzer and Sjogren, "Acta Pharm. Suec." 18:139–148, 1981).

Granules containing AD and L-carnitine-L-tartrate in a weight ratio of about 1:6 were found to be compatible with most lubricants. However, such granules were not fully chemically compatible with 0.5% magnesium stearate. For intermediate compositions and formulations containing such granules, magnesium stearate is not a preferred lubricant. Magnesium stearate is compatible with AD or L-carnitine-L-tartrate individually.

One or more glidants, such as silicon dioxide, are optionally present at a level of about 0.25–5%, usually about 0.25–1% when present, to facilitate flow of powdered components. Glidants may be added early in the process of mixing invention composition components. Thus, a glidant may be used to facilitate mixing of, e.g., AD with the alkaline excipient or other excipients.

Intermediate compositions and formulations optionally contain coloring agents, water soluble dyes, or pigments such as a synthetic iron oxide reagent, e.g., Sicopharm™ Yellow 10 or Sicopharm™ Brown 70 (Colorcon, West Point, Pa.), at about 0.1–0.2%, e.g., at about 0.15%. The tablets may optionally contain scavengers, such as lysine or gelatin, to trap formaldehyde that may be released on storage of AD. Preferably, scavengers are not present.

Excipients have been described, e.g., Monograph for "Pregelatinized Starch", Handbook of Pharmaceutical Excipients, Second Edition, American Pharmaceutical Association, 1994, pp: 491–493; Monograph for "Croscarmellose Sodium", Handbook of Pharmaceutical Excipients, Second Edition, American Pharmaceutical Association, 1994, pp: 141–142; Monograph for "Povidone", Handbook of Pharmaceutical Excipients, Second Edition, American Pharmaceutical Association, 1994, pp: 392–401; Monograph for "Crospovidone", Handbook of Pharmaceutical Excipients, Second Edition, American Pharmaceutical Association, 1994, pp: 143–144; Monograph for "Lactose Monohydrate and Anhydrous Lactose", Handbook of Pharmaceutical Excipients, Second Edition, American Pharmaceutical Association, 1994, pp: 252–261; Monograph for "Talc", Handbook of Pharmaceutical Excipients, Second Edition, American Pharmaceutical Association, 1994, pp: 519–521; Monograph for "Magnesium Stearate", Handbook of Pharmaceutical Excipients, Second Edition, American Pharmaceutical Association, 1994, pp: 280–282; Monograph for "Silicon Dioxide", Handbook of Pharmaceutical Excipients, Second Edition, American Pharmaceutical Association, 1994, pp: 424–427; Monograph for "Microcrystalline Cellulose", Handbook of Pharmaceutical Excipients, Second Edition, American Pharmaceutical Association, 1994, pp: 84–87; Monograph for "Hydrogenated Vegetable Oil, Type I", Handbook of Pharmaceutical Excipients, Second Edition, American Pharmaceutical Association, 1994, pp: 544–545.

Invention formulations include ones suitable for oral administration. The formulations are typically in unit dosage form and are prepared by any of the methods well known in the art of pharmacy. Such methods include the step of bringing AD, which is optionally present with other excipients, in contact with the alkaline excipient. In general, the formulations are prepared by uniformly and intimately bringing into association AD and the alkaline excipient with either liquid carriers or finely divided solid excipient(s) or both, and then, if necessary, drying, compressing or shaping the product.

Unit dosage formulations are made by wet granulation or by direct compression. Tablets or capsules are typically made by wet granulation of AD, an alkaline excipient and usually one or more additional excipients, followed by wet milling if necessary to obtain granules of a desired size. The granules are then dried to an LOD at 75° C. of about 2% or less, usually to about 1.5% or less. Wet granulation is accomplished using water or organic liquids such as acetone, di-n-butyl ether or alcohols containing about 1–8 carbon atoms, e.g., methanol, ethanol, n-propanol, i-propanol, n-butanol, i-butanol, t-butanol, n-pentanol, i-pentanol or a mixture thereof. Fluid bed drying is preferred over tray drying due to its shorter and more efficient drying time. Water is generally used in wet granulation manufacturing methods.

The amount of solvent in the wet granulation process is usually about 5–50% of the weight of dry components. Intermediate compositions in wet granulation processes typically have an LOD at 75° C. of about 5% or more before drying, i.e., about 5–50%. In intermediate compositions that do not contain L-carnitine-L-tartrate, the amount of solvent used is usually about 35–45% of the weight of dry components. For example, an intermediate composition may comprise about 40% solvent, such as 16 kg water in a batch that comprises 40 kg of dry composition containing AD, an alkaline excipient and optional additional excipients. When L-carnitine-L-tartrate is present, the amount of solvent is usually about 5–10% of the weight of dry components.

In general, when wet granulation is used to make invention compositions, the intragranular components comprise AD, an alkaline excipient, a diluent, a disintegrant and a binder. When lactose, lactose monohydrate or L-carnitine-L-tartrate is used as a diluent, typically about 50–70% of the total diluent, usually about 45–55%, is present as an intragranular component. Generally, granules from wet granulation are milled then added to the blender, followed by addition of the extragranular components, except for the lubricant. The lubricant is usually added last after all other components have been blended together. Intragranular components usually do not comprise a lubricant. The order of addition of intragranular components before addition of solvent is not critical and can vary. However, the dry intragranular components are thoroughly mixed before solvent is added. Mixing is usually accomplished using a high shear mixer set at a slow mixing speed for about 1–3 minutes. Once the dry components are mixed, solvent is added over about 3–8 minutes while the components are mixing, followed by additional mixing in a high shear mixer set at a slow mixing speed for about 0–2 minutes. After mixing, the wet components are milled through a #4 mesh screen or equivalent and dried, and the dried material is milled to a desired geometric mean particle size. Usually the dried material is milled to about 200–500 $\mu$m. This details of procedure may be modified to allow the use of other equipment for different size preparations. Wet granulation methods have been described, e.g., H. A. Lieberman et al, editors, *Pharmaceutical Dosage Forms*, 2nd edition, volume 1, chapter 3, pages 131–197, 1989, Marcel Dekker, Inc., New York; J. T. Carstensen, *Pharmaceutical Principles of Solid Dosage Forms*, chapter 6, pages 95–104, 1992, Technomic Publishing Co., Lancaster, Pa.

Extragranular components typically comprise a diluent, a disintegrant and a lubricant. A glidant may also be present. For example, one can prepare a 10 kg batch by mixing the granules from wet granulation and extragranular components, except the lubricant. The lubricant is added last and is mixed with other components at, e.g., about 3–5 minutes in a blender.

When microcrystalline cellulose is used as a diluent, typically about 20–60% of the total diluent, usually about 20–40%, is present as an intragranular component and the extragranular components comprise the remaining portion. The low moisture grade of microcrystalline cellulose such as Avicel™ PH-112 (FMC Corporation) is preferred for use in the extragranular portion to reduce the tablet LOD and increase tablet stability. Intragranular components usually have a geometric mean particle size of about 50–200 $\mu$m when purchased or they are milled to about that size. Dry intragranular and extragranular components are mixed, usually in a high shear mixer set at a high mixing speed for about 3–15 minutes. The mixed components are then compressed or molded as desired. The compression process may be conducted in a manner that limits friction and component heating.

In general, it is preferred to keep the temperature of the bulk of intermediate compositions below the melting point of the AD crystals, e.g., about 85–90° C. for anhydrous crystals or about 65–70° C. for AD.2H$_2$O crystals. Local regions that are transiently at a higher temperature may exist during compression or tabletting. Friction is usually also reduced by using a lubricant in invention compositions. In general, lubricant is added as the last component that is combined with other components.

Direct compression methods to make invention compositions comprise contacting dry AD, alkaline excipient, and other excipients and mixing in a high shear mixer. Individual components may be added one at a time and mixed. Alternatively, two or three components are added together and mixed before addition of one or more components, which are then mixed with the initial group of excipients. In general, components used in direct compression methods have a geometric mean particle size of about 50–300 $\mu$m or less. The order of addition of components is not critical and can vary, except that lubricant is usually added last after other components are fully mixed and it is mixed with the other components for about 3–5 minutes. In one embodiment, one adds AD, alkaline excipient and diluent together and then mixes these components. The remaining components are then added and mixed one at a time. In other embodiments, AD and alkaline excipient are mixed separately from the remaining components, and then all components are mixed together. Mixing times are typically about 3–15 minutes, depending on the size of the batch, with longer times being used for larger batches, e.g., 10–50 kg. Once the dry components are fully mixed, the resulting powder blends are typically compressed or molded, usually into unit dosages. Direct compression and theoretical considerations in mixing powders have been described, e.g., U.S. Pat. Nos. 3,873,694; 4,072,535; D. Chulia et al. editors,

*Handbook of Powder Technology*, volume 9, chapters 5, 10, 11, pages 115–161, 347–357, 359–393, 1994, Elsevier, Amsterdam.

Invention embodiments include the product made by a process of combining, mixing, compressing or otherwise contacting AD and an alkaline excipient. Such products are produced by routine methods of contacting AD and the alkaline excipient. Such products optionally also contain a diluent, a disintegrant and a binder, or other excipients described herein or in references cited herein.

Embodiments include powders, formed articles or unit dosage forms, e.g., tablets, comprising (1) about 3–30% AD, about 1–6% magnesium carbonate or calcium carbonate, about 3–8% croscarmellose sodium or crospovidone, about 3–8% pregelatinized starch or povidone, about 0–1% glidant, about 16–79.5% lactose anhydrous or lactose monohydrate, about 10–30% microcrystalline cellulose, and about 0.5–1% lubricant; (2) about 10–20% AD, about 1.5–6% alkaline excipient, about 6% disintegrant, about 5% binder, about 0–1% glidant, about 40–77% lactose, about 0–15% microcrystalline cellulose, about 0–6% talc, and about 0.5–1% lubricant; (3) about 10–30% AD, about 10–20% magnesium carbonate or calcium carbonate, about 4% croscarmellose sodium, about 0–1% glidant, about 8–45% filler, about 30% microcrystalline cellulose, about 0–6% talc, and about 1% magnesium stearate; (4) about 30–50% AD, about 6–10% magnesium carbonate or calcium carbonate, about 4–8% croscarmellose sodium, about 4–8% pregelatinized starch, about 0–1% silicon dioxide, about 16–55.5% lactose, about 0–6% talc, and about 0.5–1% lubricant; (5) 5–20 mg AD, 1–5 mg magnesium carbonate, 5–9 mg croscarmellose sodium, 5–9 mg pregelatinized starch, 0–83.5 mg lactose, 25–75 mg microcrystalline cellulose, 0–6 mg talc, and 0.5–1 mg magnesium stearate; (6) 10–30 mg AD, 3–10 mg magnesium carbonate or calcium carbonate, 6–14 mg croscarmellose sodium, 6–14 mg pregelatinized starch, 60–144 mg lactose, 30–60 mg microcrystalline cellulose, 0–10 mg talc, and 1–2 mg magnesium stearate; (7) 30–60 mg AD, 5–10 mg magnesium carbonate, 9 mg croscarmellose sodium, 7.5 mg pregelatinized starch, 0–2 mg silicon dioxide, 28.5–97.75 mg lactose, 0–22.5 mg microcrystalline cellulose, 0–9 mg talc, and 0.75–1.5 mg magnesium stearate; (8) 60–120 mg AD, 12–48 mg magnesium carbonate, 16–32 mg croscarmellose sodium, 16–32 mg pregelatinized starch, 140–294 mg lactose, 0–24 mg talc, and 2–4 mg magnesium stearate; (9) about 30 mg of AD, about 5–9 mg magnesium carbonate, about 61.5–75 mg lactose monohydrate or anhydrous lactose, about 22.5 mg of microcrystalline cellulose, about 7.5 mg of pregelatinized starch, about 9 mg of croscarmellose sodium, about 0–9 mg talc and about 0.75–1.5 mg magnesium stearate; (10) about 60 mg of AD, about 12 mg magnesium carbonate, about 70–147 mg lactose monohydrate or anhydrous lactose, about 0–60 mg of microcrystalline cellulose, about 16 mg of pregelatinized starch, about 16 mg of croscarmellose sodium, about 0–12 mg talc and about 2–4 mg magnesium stearate; and (11) about 120 mg of AD, about 24 mg magnesium carbonate, about 160–294 mg lactose monohydrate or anhydrous lactose, about 0–60 mg of microcrystalline cellulose, about 32 mg of pregelatinized starch, about 32 mg of croscarmellose sodium, about 0–24 mg talc and about 2–4 mg magnesium stearate.

Embodiments include (1) the product made by the process of contacting AD, an alkaline excipient and optionally one or more of the excipients recited herein and specifically in the paragraph immediately above and (2) the product made by the process of compressing any of these invention compositions, which are present as a powder with all components mixed together. Typically such compression is used to form tablets. The products may be produced by routine variation of the contacting process, e.g., contacting AD and an alkaline excipient in the presence or absence of another excipient(s).

Other embodiments include the product obtained by storage of AD formulations or unit dosage forms at about 15–30° C. in hermetically or induction sealed containers for about 5 or more days, e.g., storage for about 30 days to about 2 years at about 15–30° C. in sealed containers optionally containing silica gel. The specification and claims disclose exemplary suitable formulations and unit dosage forms for these embodiments.

Other embodiments include powders, formed articles or unit dosage forms, e.g., tablets, comprising about 20–65% L-carnitine-L-tartrate or L-carnitine-L-fumarate, about 4–20% AD and about 1–6% alkaline excipient. Usually L-carnitine-L-tartrate is present at about 55% or less in unit dosages such as tablets. Formulations comprising L-carnitine-L-tartrate are prepared by wet granulation or by direct compression. Invention formulations include formulations, such as unit dosages, e.g., tablets, comprising (1) about 4–20% AD, about 20–50% L-carnitine-L-tartrate, about 1–6% magnesium carbonate or calcium carbonate, about 2–6% croscarmellose sodium or crospovidone, about 13–72.5% microcrystalline cellulose, and about 0.5–5% lubricant; (2) about 4% AD, about 24–48% L-carnitine-L-tartrate, about 1–2% alkaline excipient, about 2–6% disintegrant, about 4–8% binder, about 26–64.5% microcrystalline cellulose, about 0–4% talc, and about 0.5–2% lubricant; (3) about 7.5% AD, about 45% L-carnitine-L-tartrate, about 2% magnesium carbonate, about 4% croscarmellose sodium, about 5% pregelatinized starch or povidone, about 29.5–36% filler, about 0–6% talc, and about 0.5–1% sodium stearyl fumarate; (4) about 7.5% AD, about 45% L-carnitine-L-tartrate, about 2% magnesium carbonate or calcium carbonate, about 4% croscarmellose sodium, about 5% pregelatinized starch, about 0–1% glidant, about 31.3–35% microcrystalline cellulose, about 0–0.2% iron oxide pigment, about 1–3% talc, and about 0.5–1% hydrogenated vegetable oil, type I; (5) about 4–10% AD, about 24–60% L-carnitine-L-tartrate, about 5–20% alkaline excipient, about 4% croscarmellose sodium, about 0–1% glidant, about 2–62.5% microcrystalline cellulose, about 0–2% talc, and about 0.5–1% hydrogenated vegetable oil, type I; (6) 5–30 mg AD, 30–180 mg L-carnitine-L-tartrate, 1–9 mg magnesium carbonate, 16 mg croscarmellose sodium, 20 mg pregelatinized starch, 0–209.5 mg lactose, 116 mg microcrystalline cellulose, 0.5–1 mg iron oxide pigment, 0–24 mg talc, and 2–4 mg sodium stearyl fumarate; (7) 30 mg AD, 180 mg L-carnitine-L-tartrate, 8 mg magnesium carbonate or calcium carbonate, 16 mg croscarmellose sodium, 20 mg povidone, 135.4 mg microcrystalline cellulose, 0.6 mg iron oxide pigment, 8 mg talc, and 2 mg hydrogenated vegetable oil, type I; (8) 30–60 mg AD, 180–360 mg L-carnitine-L-tartrate, 5–20 mg magnesium carbonate, 25–35 mg croscarmellose sodium, 40–50 mg pregelatinized starch, 0–271 mg lactose, 245 mg microcrystalline cellulose, 0–20 mg talc, and 4–10 mg hydrogenated vegetable oil, type I; (9) 60–120 mg AD, 360–720 mg L-carnitine-L-tartrate, 10–30 mg magnesium carbonate, 45–55 mg croscarmellose sodium, 60–70 mg pregelatinized starch, 360–860 mg microcrystalline cellulose, 0–30 mg talc, and 5–15 mg hydrogenated vegetable oil, type I or sodium stearyl fumarate; (10) 400 mg tablets containing 30 mg AD and 160–200 mg L-carnitine-L-tartrate and (11) 800 mg tablets containing 60 mg AD and 320–400 mg L-carnitine-L-tartrate. These formulations are usually prepared by wet granulation, e.g., using about 5–10% water.

Embodiments include (1) the product made by the process of contacting AD, an alkaline excipient, L-carnitine-L-tartrate and optionally one or more of the excipients recited herein and specifically in the paragraph immediately above and (2) the product made by the process of compressing any of these invention compositions, which are present as a powder with all components mixed together. Typically such compression is used to form tablets.

Typical containers for storage of the invention formulations will limit the amount of water that reaches the formulations contained therein. Typically, formulations or dosages are packaged in hermetically or induction sealed containers with a desiccant such as silica gel. Formulations can also be packaged with silica gel, activated carbon or both, but activated carbon will usually not be present. The containers are usually induction sealed. Silica gel, about 1–2 g, usually about 1 g, alone is a sufficient desiccant for storage of tablets or capsules in sealed containers containing invention formulations, usually about 30–60 tablets or capsules, at room temperature. Water permeation characteristics of containers have been described, e.g., Chapter <671>, Containers—Permeation, USP 23, United States Pharmacopeial Convention, Inc., 12601 Twinbrook Parkway, Rockville, Md. 20852, pp: 1787 et seq. (1995).

Tablets may be prepared by compressing or molding a dry powdered intermediate composition, a powder blend or granules, which are usually mixed with other excipients, e.g., binder, lubricant, diluent, disintegrant, surface active or dispersing agent. The tablets may optionally be coated and printed, embossed, or scored and may be formulated to provide either immediate or slow or controlled release of the AD therein. Invention embodiments include unit dosages such as tablets that provide a daily dose or a daily sub-dose. Invention embodiments include immediate release tablets, which usually allow conversion of at least about 90% of the AD in an oral unit dosage to a biologically absorbable form within about 45–120 minutes after ingestion by humans or animals. In slow release tablets, this conversion to a biologically absorbable form will usually occur within about 2–4 hours after ingestion. Controlled release tablets will typically release biologically absorbable AD over a period of about 1–8 hours. Immediate release formulations are typically used due to the relatively long biological in vivo half-life of PMEA, the parent drug of AD. Scored and coated tablets have been described, e.g., U.S. Pat. Nos. 5,756,124 and 5,756,123. Slow and controlled release compositions have been used to reduce the frequency of dosing and such compositions have been described, e.g., U.S. Pat. Nos. 4,810,501 and 5,316,774.

Tablets may contain a layer or region that contains AD and another region or layer that lacks AD. Such "layer" units or tablets may be used to prepare dosages that contain relatively small amounts of AD, i.e., about 1–10 mg per unit dosage. Layer tablets will usually comprise two, or at most, three 25 layers. This allows one to make low dosage units having a layer with AD at a relatively high proportion within the layer that contains AD, e.g., ≧about 5–15%. The layer usually contains one or more excipients, e.g., a diluent or a binder, in addition to the AD that is present. Alternatively a layer may comprise an excipient such as L-carnitine-L-tartrate and optionally one or more other excipients in a layer that does not contain AD, while the remaining components and AD are present in the remainder of the composition.

In addition to the components particularly mentioned above the formulations of this invention may include other agents conventional in the art having regard to the type of formulation in question, for example those suitable for oral administration may include flavoring agents, e.g., aspartame.

The present invention further provides veterinary compositions comprising AD and an alkaline excipient together with a veterinary carrier therefor.

Veterinary carriers are materials useful for the purpose of administering the composition to cats, dogs, horses, rabbits and other animals and may be solid, liquid or gaseous materials which are otherwise inert or acceptable in the veterinary art and are compatible with AD. These veterinary compositions may be administered orally, parenterally or by any other desired route.

AD present in solid invention formulations is believed to be present as crystalline AD with little or no detectable amorphous AD, i.e., ≦about 10–20% amorphous AD. The crystalline AD in invention formulations is believed to comprise at least about 85% anhydrous crystals and less than about 15% AD.2H$_2$O crystals or amorphous AD. AD.2H$_2$O may arise from adding water to anhydrous crystals during wet granulation. Diagram A below shows a representative process flow diagram for making AD and anhydrous AD crystals.

Diagram A

(EtO)$_2$P(O)H step1
1. (CH$_2$O)$_n$/Et$_3$N
2. p-TsCl (EtO)$_2$P(O)—CH$_2$—OTs step 2
adenine
DMF
NaOH

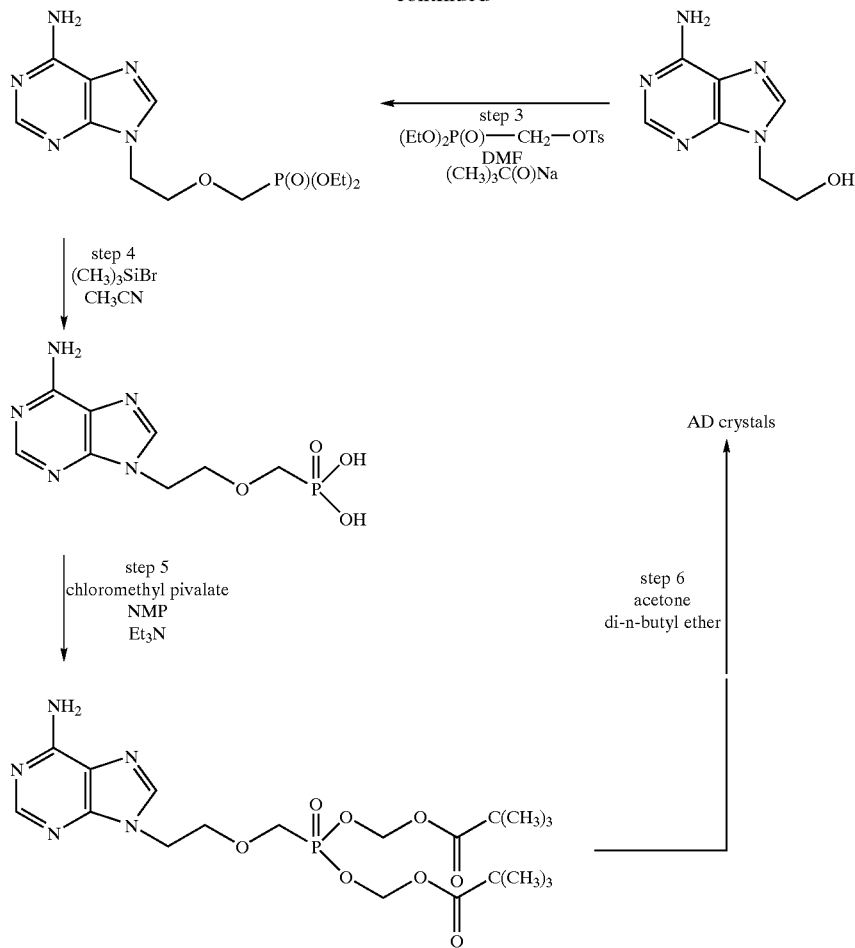

One can increase or decrease the scale of the process steps shown in Diagram A and described below if desired.

Methods for Diethyl p-toluenesulfonyloxymethylphosphonate Synthesis

In an embodiment, synthesis of diethyl p-toluenesulfonyloxymethylphosphonate, shown in Diagram A, Step 1, is described as follows. In a reactor having an inert atmosphere, e.g., nitrogen, a mixture of diethylphosphite (0.8 kg), paraformaldehyde (0.22 kg), and triethylamine (0.06 kg) in toluene (2.69 kg) is heated to 87° C. (84 to 110° C.) for 2 hours with agitation, then heated to reflux and maintained for at reflux for 1 hour, until the reaction is complete. Reaction completion is monitored by TLC (trace or no diethyl phosphite detectable) and confirmed by $^1$H NMR showing no more than 1% of the diethyl phosphite peak at δ 8.4–8.6 ppm. The solution is cooled to about 1° C. (−2 to 4° C.) and p-toluenesulfonyl chloride (1.0 kg) is added and then triethylamine (0.82 kg) at no more than 10° C. is slowly added (over about 3–6 hours in an exothermic reaction). The resulting mixture is warmed to 22° C. (19–25° C.) and stirred for at least 5 hours (typically about 16–24 hours), until the reaction is complete. Reaction completion is monitored by TLC (trace or no p-toluenesulfonyl chloride detectable) and confirmed by $^1$H NMR (p-toluenesulfonyl chloride doublet at δ 7.9 ppm no longer detected). The solids are removed by filtration and rinsed with toluene (0.34 kg). The combined washings and filtrate are washed either twice with water (1.15 kg each), or optionally with a sequence of water (1.15 kg), 5% aqueous sodium carbonate (3.38 kg), and twice with water (1.15 kg each). In the event emulsion occurs, brine may be added to the first organic/water mixture. The organic phase, which is at no more than 50° C., is distilled in vacuo (to LOD no more than 10% and water content, by KF (Karl Fischer) titration, no more than 0.5%), affording the title compound as an oil of about 85–95% purity, exclusive of toluene. The oil may become viscous on cooling.

Methods for 9-(2-Hydroxyethyl)adenine Synthesis

In an embodiment, synthesis of 9-(2-hydroxyethyl) adenine, shown in Diagram A, Step 2, is described as follows. In a reactor having an inert atmosphere, e.g., nitrogen, sodium hydroxide (6 g) is added to a slurry of adenine (1.0 kg) and molten ethylene carbonate (0.72 kg, m.p. 37–39° C.), in 2.5 kg dimethylformamide (DMF) and the mixture is heated to 125° C. (95° C. to reflux) with agitation until the reaction is complete (about 3–9 hours if the mixture temperature is at 110° C. to reflux or about 15–48 hours if at 95 to 110° C.). Reaction completion is monitored by HPLC (no more than 0.5% adenine remaining). The mixture is cooled to below 50° C. and diluted with toluene (3.2 kg). The resulting slurry is cooled to 3° C. (0–6° C.) and agitated for at least 2 hours. The slurry is filtered and the filter cake is washed twice with cold (0–5° C.) toluene (0.6 kg each). The filter cake is dried in vacuo at 35 to 70° C. (no more than 2% toluene, by $^1$H NMR or LOD) and optionally milled, affording the title compound as a white to off-white powdery solid.

Methods for 9-[2-(Diethylphosphonomethoxy)ethyl] adenine Synthesis

In an embodiment, synthesis of 9-[2-(diethylphosphonomethoxy)-ethyl]adenine, shown in Diagram A, Step 3, is described as follows. In a reactor having an inert atmosphere, e.g., nitrogen, a slurry of 9-(2-hydroxyethyl)adenine (1.0 kg) and DMF (4.79 kg) is warmed to about 130° (125–135°) for 30–60 minutes. The reactor contents are rapidly cooled with vigorous agitation to about 25° (20–30°) and sodium t-butoxide (0.939 kg) is added in portions over about 1–3 hours while maintaining vigorous agitation and the contents temperature at about 25° (20–30°). The agitation and temperature is maintained for about 15–45 minutes after all sodium t-butoxide has been added. Then the reactor contents are cooled to about −10° (−13 to 0°) and a solution of diethyl p-toluenesulfonyloxymethyl-phosphonate (2.25 kg on a pure basis) in DMF (1.22 kg) is added over about 5–10 hours. The mixture is kept at about −5° (−10 to 0°) until the reaction is complete, which is typically about 0.5–2 hours after the final portion of diethyl p-toluenesulfonyloxymethyl-phosphonate has been added. Reaction completion is monitored by HPLC (not more than 3% 9-(2-hydroxyethyl)adenine remaining). Glacial acetic acid (0.67 kg) is added, with the pot temperature controlled to no more than 20°. The mixture at about 22° (15–25°) is agitated for about 15–45 minutes. The quenched mixture is concentrated in vacuo until distillation stops and the contents are then cooled to below 40°. Dichloromethane (16.0 kg) is added and the contents at 20° (15–25°) are agitated for at least 1 hour. If the DMF content versus total solids (NaOTs (sodium tosylate), NaOAc, Et$_2$PMEA) is greater than 20% (by $^1$H NMR) the mixture is concentrated in vacuo until distillation stops, the contents are cooled to below 40° C., dichloromethane (16 kg) is added and the reactor contents at about 20° (15–25°) are agitated for at least 1 hour. Diatomaceous earth (0.5 kg) is added and the contents, which are at about 20° (15–25°), are agitated for at least 1 hour. The solids are removed by filtration and rinsed 3 times with CH$_2$Cl$_2$ (about 1 kg each). The filtrate and rinses at no more than 80° are concentrated in vacuo until distillation stops, the reactor contents are cooled to below 40°, dichloromethane (5.0 kg) is added to the residue and the contents at about 25° (20–40°) are agitated to dissolve the solids. The resulting solution at no more than 80° is concentrated in vacuo until distillation stops. Dichloromethane (7.0 kg) is added and the contents at about 25° (20–40°) are agitated to dissolve the solids. If the DMF content compared to diethyl PMEA is greater than 12%, the mixture at no more than 80° is concentrated in vacuo, the contents are cooled to below 40°, dichloromethane (7.0 kg) is added and the contents at about 25° (20–40°) are agitated to dissolve the solids. The mixture is washed with water (0.8 kg) at about 25° (22–30°) by agitating for about 15–45 minutes. The phases are allowed to separate for 4 hours and the phases are then separated. The aqueous phase is back-extracted twice with dichloromethane (1.5 kg per wash) by agitation for about 15–45 minutes with the solution maintained at about 25° (22–30°), followed by allowing the phases to separate for at least 2 hours. The combined organics at no more than 80° are then concentrated in vacuo until distillation stops. Toluene (3.0 kg) is added, agitated at about 25° (22–30°) for about 15–45 minutes and the resulting mixture at no more than 80° is azeotroped in vacuo. Toluene (3.0 kg) is added and the mixture is heated to about 80° (75–85°), agitated for about 15–45 minutes, cooled to below 30° over about 60–90 minutes and then cooled to about 0° (−3 to 6°). After at least 12 hours at about 0 with slow agitation, the resulting slurry is filtered and the filter cake is rinsed three times with cold (about 0–6°) toluene (about 0.2 kg per rinse). The wet cake is dried in vacuo at about 50° (35 to 65°) and the dried product is milled. Product drying is monitored for water removal (no more than 0.3% water detected by KF titration). The inert atmosphere is maintained throughout step 3.

Methods for PMEA Synthesis

In an embodiment, synthesis of PMEA, shown in Diagram A, Step 4, is described as follows. In a reactor having an inert atmosphere, e.g., nitrogen, a mixture of diethyl PMEA (1.00 kg), acetonitrile (2.00 kg), and bromotrimethylsilane (1.63 kg) is heated to and maintained at reflux for about 1–3 hours with agitation, until the reaction is complete. Reaction completion is monitored by $^{31}$P NMR or HPLC (no diethyl PMEA and no more than 2% monoethyl PMEA detected). The solution at ≦80° C. is distilled in vacuo to a semi-solid, which is taken up in water (2.00 kg) and warmed to about 55° C. (52–58° C.) for about 30–60 minutes with agitation to dissolve all solids. The resulting mixture is cooled to about 22° C. (19–25° C.), adjusted to pH 3.2 with aqueous sodium hydroxide, the contents are heated to about 75° C. (72–78° C.) until the consistency thins (about 15–120 minutes), cooled to about 3° C. (0–6° C.), and stirred for at least 3 hours (3–6 hours). The slurry is filtered and the filter cake is rinsed with water (1.00 kg). The wet cake is suspended in water (3.75 kg) and the suspension is heated to about 75° C. (72–78° C.) with vigorous stirring. After stirring for about 2 hours, the slurry is cooled to about 3° C. (0–6° C.) and stirred for at least another 2 hours. The slurry is filtered and the filter cake is rinsed sequentially with two portions of water (0.50 kg per rinse) and two portions of acetone (1.00 kg per rinse). The isolated solid is dried in vacuo at no more than about 90° C. to a low water content (no more than 0.5% water detected by KF titration), to provide PMEA as white crystals. The product is milled to a fine particle size.

Methods for AD Synthesis

An exemplary method to prepare AD comprises suspending 1 molar equivalent of PMEA in a volume of about 5.68–56.8 equivalents of NMP/equivalent PMEA and, after one suspends the PMEA, adding about 2–5 molar equivalents, often about 2.5–3.5, usually about 3 molar equivalents, of triethylamine ("TEA") to the solution using mild to moderate agitation. One then adds about 3–6 molar equivalents, often about 4.5–5.5 molar equivalents, usually about 5 equivalents, of chloromethyl pivalate to obtain a reaction mixture. The reaction mixture is usually prepared at room temperature. One heats the reaction mixture to maintain a temperature of less than 66°, typically about 28–65°, usually between about 55–65° for about 2–4 hours to conduct the reaction. The time needed to heat the reaction mixture to about 28–65° is not critical and can vary depending on the reaction mixture volume and the capacity of the apparatus used to heat the mixture. Mild or moderate agitation maintains solids in suspension during the reaction and this minimizes extensive splashing of the reactants in the reaction vessel. This method results in a product comprising AD produced by the process of reacting the listed reactants, typically under the given conditions.

In an embodiment, conversion of PMEA to AD, shown in Diagram A, Step 5, is described as follows. In a reactor having an inert atmosphere, e.g., nitrogen, a mixture of 1-methyl-2-pyrrolidinone (3.15 kg), PMEA (1.00 kg), triethylamine (1.11 kg), and chloromethyl pivalate (2.76 kg) is heated to about 60±3° C. (no more than 66° C.) and stirred using moderate agitation for ≦4 hours (1–4 hours) until the reaction is complete, as indicated by $^{31}$P NMR or HPLC (no more than 15% mono(POM)PMEA). The mixture is diluted with isopropyl acetate (12.00 kg), cooled to 25±3° C., and agitated for about 30 minutes. The solids are removed by filtration and washed with isopropyl acetate (5.0 kg). The combined organics are washed twice with water (3.70 kg per wash) by moderately agitating the mixture at a mixture temperature of 25±3° C. for about 15–45 minutes. The combined aqueous washes are back-extracted twice with isopropyl acetate (4.00 kg per extraction) at a mixture temperature of 25±3° C. by agitation for 15–45 minutes. The combined organics are washed with water (1.80 kg) by agitation for 15–45 minutes and then the organics at about 35±5° C. (no more than 40° C.) are concentrated in vacuo to approximately 40% of the original volume. After a polishing filtration (1 μm filter), and a rinse forward with 1.5 kg of isopropyl acetate, the concentration of the organics in vacuo is resumed until a pale oil remains the organics at about 35±5° C. (no more than 50° C.). The oil typically comprises about 6–45% AD, usually about 30–42%.

Methods for AD Crystallization

AD Crystallization from the organic oil is usually accomplished by (1) using a relatively low volume of NMP in the AD synthesis reaction as compared to the amount of PMEA present as a reactant, i.e., less than about 10 mL NMP per gram PMEA, and/or (2) by minimizing the amount of isopropyl acetate that remains entrained in the organic oil after vacuum distillation by allowing sufficient time for vacuum distillation, i.e., usually at least about 4–6 hours. The aggregate of reaction starting materials, e.g., NMP or PMEA, in the oil can account for about 2–20% of the crystallization solution, but generally less than about 1–2%. When crystals are prepared from organic oil, about 20–45%, often about 30–42%, and usually about 35–42% of AD is present in the oil before adding crystallization solvents.

One optionally crystallizes AD optionally from a supersaturated solution. Nucleation occurs in such supersaturated solutions, and readily leads to crystal formation. Nucleation rates typically increase when the degree of supersaturation and the temperature increases. Supersaturated solutions typically are prepared by changing the temperature (usually decreasing it), solvent evaporation or altering solvent composition, e.g., by adding a miscible nonsolvent or poor solvent. Combinations of these methods also generate supersaturated AD solutions, e.g., using evaporation under reduced pressure to both cool the solution while increasing the solute concentration.

Crystalline AD is prepared by allowing crystal formation in an AD composition, usually from a solution of AD in a crystallization mixture containing at least about 6%, typically at least about 30%, usually at least about 35%, of AD. One would ordinarily conduct crystallizations by preparing an AD solution comprising about 6–45% AD and about 55–94% crystallization solvent. The upper limit of solubility of AD is about 10–41% for most crystallization solvents at room temperature. AD is not freely soluble in some crystallization solvents, e.g., AD solubility in di-n-butyl ether is less than about 0.3 mg/mL, and adding these solvents to an AD solution increases the degree of saturation or supersaturation of the solution. One usually uses organic solutions containing an amount of AD that is near the upper solubility limit in the crystallization solvent(s). The lower amount, about 6%, is the minimum amount of AD needed in a solution to consistently yield crystals. Certain solvents, e.g., methanol or $CH_2Cl_2$, can contain more than about 50% AD.

The temperature at which crystallization is conducted is not critical and can vary, as the crystallization process usually proceeds spontaneously over a range of temperatures. Crystallization at temperatures above about 35°, especially about 45–50° may result in reduced yield and/or in an increase in impurities associated with the crystals. Crystallizations are generally conducted at temperature ranges of about −5° to about 50°, often about 0–35°, usually about 4–23°. One can optionally use crystallization temperatures below about −5° to increase the crystal yield or to enhance the crystal formation rate, but a low temperature process may result in increased by-products. Thus it is generally more convenient and economic to use solvents either at approximately room temperatures (about 15–23°) or at the typical cooling temperatures that most cooling apparatus or methods can easily reach (about 0–4°). When a solution contains relatively low concentrations of AD, i.e., about 10–20%, crystallization at a relatively low temperature, i.e., about 0–15° will often enhance crystal yields.

Heating the solution containing AD and crystallization solvent(s) to a point above room temperature, preferably to about 35°, appears to facilitate crystallization, presumably by increasing the nucleation rate. The time to heat the crystallization mixture to about 35° is not critical and can vary according to the capacity of the apparatus used, generally over a period of about 20–45 minutes. Heating is then discontinued and the temperature is reduced by cooling or by allowing the temperature to fall for about 10–120 minutes. During this time, crystals form and continue to form over a period of at least about 4–36 hours. Crystallization usually begins immediately or shortly after the crystallization mixture has reached 35°. Crystallizations are usually conducted by allowing the temperature to fall to about 0–23° C. after the solution reaches 35°. Crystallizations conducted with or without mild to moderate agitation, typically with mild agitation, routinely give good results.

Appreciable crystallization usually occurs over a period of about 5 minutes to about 72 hours and about 10–16 hours routinely give good results regardless of the solvents used. The time of crystallization is not critical and can vary, although relatively short crystallization times (about 30–90 minutes) may result in reduced AD recovery. When one adds crystallization solvents to reaction mixtures containing other organic solvents, e.g., NMP, crystallization usually begins immediately once the temperature has reached about 35° or less and the solution becomes hazy.

Crystallization solvents used to prepare anhydrous AD crystals generally contain less than about 0.2% of water. When a significant amount of water is present in the crystallization solvent, i.e., about 1–2%, the crystallization process yields varying amounts of $AD.2H_2O$ crystals, that are also recovered together with anhydrous AD crystals. The amount of water that is present in a crystallization reaction is optionally reduced by conventional means, including using anhydrous reagents or by drying solvents using molecular sieves or other known drying agents. One optionally reduces the amount of water that might be present in organic solutions containing AD, e.g., from AD synthesis reactions containing by-products and solvents such as the organic oil described above, by using an azeotroping co-solvent such as isopropyl acetate to reduce water prior to adding crystallization solvents.

In an embodiment, crystallization of anhydrous AD crystals, shown in Diagram A, Step 6, is described as follows. The pale oil containing AD described above is dissolved in acetone (1.0 kg), heated to 35±3° C., and diluted with di-n-butyl ether (5.00 kg) in about 4 portions while maintaining a temperature of about 32–38° C. and moderate agitation. The clear solution is cooled to about 25–30° C. over about 30–60 minutes (no more than 90 minutes), seeded with a small quantity of anhydrous AD crystals (about 5 g), and the contents are then cooled to 22±3° C. over about 30–60 minutes (no more than 90 minutes) while maintaining moderate agitation. Moderate agitation of the mixture is continued at 22±3° C. for a minimum of about 15 hours. The resulting slurry is filtered and the filter cake is washed with a premixed solution of acetone (0.27 kg) in di-n-butyl ether (2.4 kg) (1:9 v/v). The wet solids are optionally further purified by adding premixed acetone (0.57 kg) and di-n-butyl ether (4.92 kg), maintaining the temperature of the contents at 22±3° C. for about 15–24 hours with agitation. The solids are then filtered, and the filter cake is washed with premixed acetone (0.27 kg) and di-n-butyl ether (2.4 kg). The filter cake maintained at <35° C. (about 25–35° C.) is dried in vacuo for about 1–3 days (LOD no more than 0.5%), affording anhydrous AD crystals as a white to off-white powdery solid. The dried product is milled.

All citations are incorporated herein by reference in their entirety.

EXAMPLES

Example 1

AD Formulation Containing Magnesium Carbonate.

A formulation was prepared by wet granulation. The formulation contained AD (20%), lactose monohydrate (58%), pregelatinized starch (5%), croscarmellose sodium (6%), magnesium stearate (1%), talc (6%) and magnesium carbonate (4%). Magnesium carbonate was present as magnesium carbonate hydroxide, 4 $MgCO_3 \cdot Mg(OH)_2 \cdot 5\ H_2O$. The LOD measured at 75° C. of the resulting formulation was about 3% or less, usually 2% or less.

| Component | 30 mg. Tablet % w/w | 30 mg. Tablet mg/tab. | 60 mg Tablet % w/w | 60 mg Tablet mg/tab. | 120 mg Tablet % w/w | 120 mg Tablet mg/tab. |
|---|---|---|---|---|---|---|
| AD | 20.0 | 30.0 | 15.0 | 60.0 | 30.0 | 120.0 |
| Pregelatinized Starch, NF | 5.0 | 7.5 | 5.0 | 20.0 | 5.0 | 20.0 |
| Croscarmellose Sodium, NF[1] | 6.0 | 9.0 | 6.0 | 24.0 | 6.0 | 24.0 |
| Lactose Monohydrate, NF[2] | 58.0 | 87.0 | 64.0 | 256.0 | 46.0 | 184.0 |
| Magnesium Carbonate, USP/NF | 4.0 | 6.0 | 3.0 | 12.0 | 6.0 | 24.0 |
| Talc, USP | 6.0 | 9.0 | 6.0 | 24.0 | 6.0 | 24.0 |
| Magnesium Stearate, NF | 1.0 | 1.5 | 1.0 | 4.0 | 1.0 | 4.0 |
| Total | 100.0 | 150.0 | 100.0 | 400.0 | 100.0 | 400.0 |

[1]Incorporated into the dosage form in two portions (intragranular and extragranular) during manufacturing. About 50% was used for each portion.
[2]Incorporated in an intragranular portion (about 80%) and extragranular portion (about 20%)

| Component | 10 mg Tablet % w/w | 10 mg Tablet mg/tab. |
|---|---|---|
| AD | 8.0 | 10.0 |
| Pregelatinized Starch, NF | 5.0 | 6.3 |
| Croscarmellose Sodium, NF[1] | 6.0 | 7.5 |
| Lactose Monohydrate, NF[2] | 72.0 | 90.0 |
| Magnesium Carbonate, NF | 2.0 | 2.5 |
| Talc, USP | 6.0 | 7.5 |
| Magnesium Stearate, NF | 1.0 | 1.2 |
| Total | 100.0 | 125.0 |

An exemplary AD formulation with several excipients in tablets containing 10, 30, 60 or 120 mg AD per tablet was accomplished as follows. Tablets were made by blending one-half of the weight of croscarmellose sodium shown in the table, all of the magnesium carbonate, all of the pregelatinized starch and about 80% of the lactose monohydrate shown in the table in a granulator. Water was added and the contents were mixed in a granulator (Colette, Gral-10) until wet granules formed. The wet granules were milled (Co-Mil model 197S, Quadro Corp., Waterloo, Canada), dried in a fluid bed dryer (Glatt, GPCG-1) to a moisture content of not more than 2.0% LOD and the dried granules were passed through a mill (Co-Mil model 197S, Quadro Corp., Waterloo, Canada) and milled to appropriate particle size (geometric mean particle size of about 250 μm). The milled granules were combined with extragranular excipients, lactose monohydrate (the remaining 20%), croscarmellose sodium (the remaining one-half) and talc, and blended in a blender (4 quart PK V-blender) to obtain a homogenous powder blend. Magnesium stearate was added, blended, and compressed into tablets by compression of the mixture using an instrumented 16 station rotary tablet press (β-type, Manesty) using ¼–13/32 inch diameter flat-faced round punches. Tablets were compressed to a hardness ranging from 3–10 Kp for ¼ inch diameter tablets weighing ≦200 mg and 6–16 Kp for 5/16–13/32 inch diameter tablets weighing 200–400 mg. The upper punch pressure was measured periodically during each run using a data acquisition system (Model PC 30, SMI, Pittstown, N.J.). The tablets were filled into high density polyethylene or glass bottles along with polyester fiber packing material and optionally with silica gel desiccant. The bottles were then induction sealed.

Example 2

AD Formulation Containing Magnesium Carbonate and Microcrystalline Cellulose

AD and an alkaline excipient were formulated with several excipients and compressed into tablets that contained 5, 10, 30, 60 or 120 mg AD per tablet. The tablets were prepared by wet granulation in a manner similar to that described in example 1 above. Magnesium carbonate was present as magnesium carbonate hydroxide, light magnesium carbonate or as heavy magnesium carbonate in different preparations.

| Component | 5 mg % w/w | 10 mg % w/w | 30 mg % w/w | 60 mg % w/w | 120 mg % w/w |
|---|---|---|---|---|---|
| AD | 4.0 | 8.0 | 20.0 | 30.0 | 50.0 |
| Lactose Monohydrate, NF or Lactose Anhydrous, NF | 67.5 | 62.5 | 48.5 | 36.5 | 14.5 |
| Microcrystalline Cellulose, NF | 15.0 | 15.0 | 15.0 | 15.0 | 15.0 |
| Croscarmellose Sodium, NF | 6.0 | 6.0 | 6.0 | 6.0 | 6.0 |
| Pregelatinized Starch, NF | 5.0 | 5.0 | 5.0 | 5.0 | 5.0 |
| Magnesium Carbonate, USP | 1.0 | 2.0 | 4.0 | 6.0 | 8.0 |
| Silicon Dioxide, NF | 0.5 | 0.5 | 0.5 | 0.5 | 0.5 |
| Magnesium Stearate, NF | 1.0 | 1.0 | 1.0 | 1.0 | 1.0 |
| Tablet weight (mg) | 125 | 125 | 150 | 200 | 240 |

Example 3

AD Formulation Containing Calcium Carbonate

AD tablets containing an alkaline excipient were formulated as described above and tested for stability of the AD under different relative humidity and temperature conditions. AD, lactose, pregelatinized starch, 50% of the croscarmellose sodium indicated in the table below, and calcium carbonate were mixed and then wet granulated using about 30–40% water. After wet-milling, the granules were dried and milled to appropriate particle size (geometric mean particle size of about 250 µm). The granules were powder blended with the remaining 50% of croscarmellose sodium, silicon dioxide, and microcrystalline cellulose for 3–10 minutes. The powder blend was mixed with magnesium stearate for another 3–5 minutes. Tablets were prepared by compression of the mixture in a manner similar to that described in example 1 above.

| Component | 5 mg % w/w | 10 mg % w/w | 30 mg % w/w | 60 mg % w/w | 120 mg % w/w |
|---|---|---|---|---|---|
| AD | 4.0 | 8.0 | 20.0 | 30.0 | 50.0 |
| Lactose Monohydrate, NF or Lactose Anhydrous, NF | 66.5 | 60.5 | 44.5 | 31.5 | 6.5 |
| Microcrystalline Cellulose, NF | 15.0 | 15.0 | 15.0 | 15.0 | 15.0 |
| Croscarmellose Sodium, NF | 6.0 | 6.0 | 6.0 | 6.0 | 6.0 |
| Pregelatinized Starch, NF | 5.0 | 5.0 | 5.0 | 5.0 | 5.0 |
| Calcium Carbonate, USP/NF | 2.0 | 4.0 | 8.0 | 10.0 | 16.0 |
| Silicon Dioxide, NF | 0.5 | 0.5 | 0.5 | 0.5 | 0.5 |
| Magnesium Stearate, NF | 1.0 | 1.0 | 1.0 | 1.0 | 1.0 |
| Tablet weight (mg) | 125 | 125 | 150 | 200 | 240 |

Example 4

Stability of AD Formulation Containing Alkaline Excipients

Magnesium carbonate, light powder, USP/NF; calcium carbonate, light powder, USP/NF; and zinc carbonate, basic powder, reagent grade; and calcium phosphate dibasic, anhydrous powder were available from Spectrum Quality Products, Inc. (Gardena, Calif.).

Each batch of AD granules was prepared by wet granulation. The batch size was 10 g. The formulation components consisted of 15% w/w AD and 0–5% w/w alkaline excipient, a diluent (72–77% lactose monoydrate), a binder (5% pregelatinized starch), and a disintegrant (3% croscarmellose sodium). The control formulation contained 15% w/w AD with no salt.

All excipients were weighed, mixed, and passed through a #40 mesh screen (Gilson Co., Worthington, Ohio). The sieved powder then was transferred into a mortar and mixed with a pestle for one minute. Water (3.2–3.3 mL) was added slowly through a 5 mL syringe (Becton Dickinson & Co., Franklin Lakes, N.J.) equipped with a 19G 1½ inch needle (Becton Dickinson & Co.). The wet granules were mixed by a pestle and a spatula in a mortar for three minutes, passed through a #10 mesh screen, and dried in an oven at 40° C. overnight. The dried granules were ground in a mortar to fine powders for the stability testing.

A stability-indicating HPLC method was used for the potency and degradation product profile assays for AD. The HPLC assays were performed using a fully automated, computer-controlled Hewlett Packard Series II 1090 liquid chromatography (Palo Alto, Calif.). An HPLC$^{3D}$ ChemStation (Hewlett Packard) was used for data acquisition. The method used an Alltech™ mixed mode anion exchange $C_8$ column (7 micron, 100 Å pore size, 4.6×250 mm) equipped with an Alltech Direct-Connect™ refillable guard column dry-packed with Pellicular™ $C_8$ particles (2×10 mm) at room temperature with a flow rate at 1.2 mL/min and a UV detection at 260 nm. The mobile phase A consisted of 30% acetonitrile and 70% pH 6.0 (200 mM) phosphate buffer, and the mobile phase B consisted of 50% acetonitrile and 50% pH 6.0 (200 mM) phosphate buffer. The gradient profile was 100% mobile phase A for one minute, followed by a 19-minute linear gradient to 100% mobile phase B, then held at 100% mobile phase B for 5 minutes. A 10-minute equilibration at 100% mobile phase A was employed between injections. A 15 µL sample was injected to the system. The amounts of AD and degradation products were reported by area normalization.

Approximately 50 mg of granules were weighed and transferred into a 25 mL volumetric flask. Five mL of pH 2.8 (25 mM) phosphate buffer were added, and the mixture was sonicated for 15 minutes. Acetonitrile was added to the flask to approximately 1 cm below the volume marker, and the mixture was sonicated for another 15 minutes. Excessive warming was prevented during sonication. After removal of the volumetric flask from the sonicator, the mixture was allowed to equilibrate to room temperature. Acetonitrile was filled to the exact volume and mixed well. The solution was filtered through a 0.45 µm Nylon 66 membrane filter unit (Rainin), and the first 2 mL aliquot was discarded. The final concentration of AD was approximately 0.3 mg/mL.

Approximately 2 g of granules were weighed and transferred to a scintillation glass vial (Wheaton Scientific Products, Millville, N.J.). These samples were uncapped and placed in a 30% relative humidity (RH) environment chamber which was controlled by placing saturated solutions of magnesium bromide hexahydrate in a closed container. The container was stored in a 60° C. oven (Model DK-63 Constant Temperature Oven, Scientific Products, McGaw Park, Ill.). Approximately 300 mg samples were removed at each time point and stored in a refrigerator until assay.

The accelerated stability studies were conducted at 60° C. and 30% RH under open conditions to allow for direct comparison between various formulations. The open condition was selected to eliminate the role of LOD in formulations and packaging variables on the stability of AD.

Four compounds, $CaCO_3$, $MgCO_3$, $ZnCO_3$, and $CaHPO_4$, were incorporated as intragranular excipients in AD formulations. The figure below depicts the percent degradation of AD as a function of time at 60° C. and 30% RH for formulations containing 3% $CaCO_3$, 2% $MgCO_3$, 2% $ZnCO_3$, and 2% $CaHPO_4$ as compared to the control. As shown below, the most stable formulation contained 2% $MgCO_3$. $CaCO_3$ and $ZnCO_3$ also demonstrated a stabilizing effect on AD. In contrast, $CaHPO_4$, has a $pK_a$ of the conjugated acid of about 2, showed no significant improvement on AD stability compared to a control formulation.

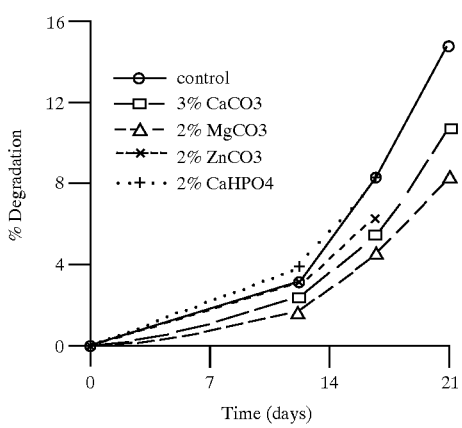

The figure shown below depicts the effect of $MgCO_3$ concentration on the extent of degradation of AD. The increase in $MgCO_3$ concentration from 0 to 3% enhanced the stability of AD, but a $MgCO_3$ concentration of 3–5% did not appear to further improve AD stability under these assay conditions.

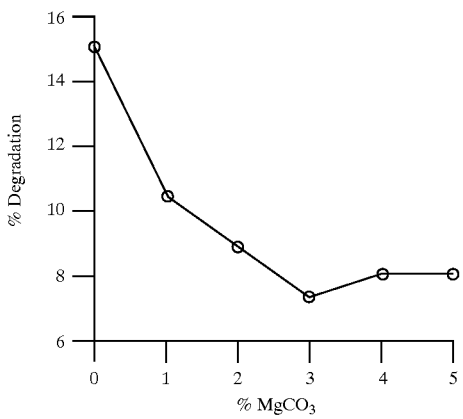

The effect of carbonates as an extragranular excipient was also studied. Two powder blends were prepared containing 2% extragranular $CaCO_3$ and $MgCO_3$. After 21 days of storage, the % AD remaining for formulations containing $CaCO_3$ (86.3%) and $MgCO_3$ (86.8%) were similar to the control formulation (86.4%), suggesting that the extragranular addition of $CaCO_3$ and $MgCO_3$ did not strongly affect the stability of AD. The product distribution of these two powder blends was similar to the control, indicating that higher amounts of alkaline excipient are needed to achieve the same effect as an intragranular alkaline excipient.

Three compounds, 2% $NaHCO_3$, 2% $Na_2CO_3$, and 2% $NaH_2PO_4$, were incorporated as an intragranular excipient in AD formulations. The stability results for these three formulations were compared to the control formulation. The results showed that AD was unstable in the presence of either $NaHCO_3$ or $Na_2CO_3$. In addition, the storage of these granules was accompanied with a color change to brown. The stability of AD granules containing $NaH_2PO_4$ was also compromised. The effect of de-stabilizing AD appeared to be in the order of $Na_2CO_3 > NaHCO_3 > NaH_2PO_4$.

Example 5

Direct Compression of Tablets Containing AD

AD and croscarmellose sodium were mixed for 3–10 minutes, followed by mixing with lactose and magnesium carbonate for 3–10 minutes, then mixed with microcrystalline cellulose for 3–10 minutes, followed by mixing with talc for 3–10 minutes and then mixed with magnesium stearate for another 3–10 minutes. Tablets were prepared by direct compression of the mixture using an instrumented 16 station rotary tablet press (β-type, Manesty). The tablets contained the components shown below.

| Component | 5 mg % w/w | 10 mg % w/w | 30 mg % w/w | 60 mg % w/w |
|---|---|---|---|---|
| AD | 4.0 | 8.0 | 15.0 | 20.0 |
| Lactose Monohydrate, NF | 50.0 | 40.0 | 24.0 | 19.0 |
| Microcrystalline Cellulose, NF | 30.0 | 30.0 | 30.0 | 30.0 |
| Croscarmellose Sodium, NF | 4.0 | 4.0 | 4.0 | 4.0 |
| Magnesium Carbonate, USP/NF | 5.0 | 11.0 | 20.0 | 20.0 |
| Talc, USP | 6.0 | 6.0 | 6.0 | 6.0 |
| Magnesium Stearate, NF | 1.0 | 1.0 | 1.0 | 1.0 |
| Tablet weight (mg) | 125 | 125 | 200 | 300 |

Example 6

AD Formulations Containing L-carnitine-L-tartrate

Two 10 kg (750 g of AD) batches of AD formulation containing 45% w/w L-carnitine-L-tartrate were prepared. One batch contained 2.0% w/w magnesium carbonate. The other batch contained no carbonate salt and served as a control formulation. AD, about 35% of the microcrystalline cellulose, pregelatinized starch, 50% of the croscarmellose sodium, and magnesium carbonate were mixed and then wet granulated using about 8.5% water. A high shear mixer (Niro-Fielder PMA 25, Niro-Aeromatic, Columbia, Md.) was used for wet granulation. After wet-milling (Quadro Co-Mil), the granules were dried to achieve an LOD of about 1.4% (65–70° C. for 30–60 minutes) using a Glatt GPCG-1 fluid bed dryer. The inlet, exhaust, and product temperatures were followed and recorded periodically during drying. The dried mixture was dry-milled to appropriate particle size (about 200–500 μm average particle diameter). Dry-milling was carried out using a Quadro Co-Mil (model 197S) equipped with a grated screen (2A-050G037/19136) and a 0.175 inch spacer. The milling speed was 1600 rpm.

The granules were then powder blended with the remaining 50% of croscarmellose sodium, talc, and the remaining about 65% of microcrystalline cellulose. The powder-blending was performed in a Gemco 1 cu. ft. blender. The granules were mixed with all extragranular excipients except the hydrogenated vegetable oil lubricant for 5 minutes. After addition of the lubricant, the final powder blend was mixed for another 5 minutes.

Tablets were then compressed into tablets on an instrumented 16 station rotary tablet press (β-type, Manesty) using 0.3480"×0.6975" diameter capsule shaped punches. The punches were placed at alternate positions on the turret, and the β-press was operated at the slowest turret speed to maximize the total tabletting time. The tablets were compressed to a hardness ranging from 12–16 Kp. The upper punch pressure was measured periodically during each run using a data acquisition system (Model PC 30, SMI, Pittstown, N.J.). Tablet samples were collected periodically to check the tablet weight and tablet hardness.

The other strength of AD and L-carnitine-L-tartrate tablets was prepared in a similar method as described above, and the compositions of different strength of AD and L-carnitine-L-tartrate tablets are summarized in the following table.

| Component | 5 mg % w/w | 10 mg % w/w | 30 mg % w/w | 60 mg % w/w |
|---|---|---|---|---|
| AD | 4.0 | 6.7 | 7.5 | 7.5 |
| L-Carnitine-L-Tartrate | 24.0 | 49.3 | 45.0 | 45.0 |
| Microcrystalline Cellulose, NF | 59.0 | 30.0 | 33.5 | 33.5 |
| Croscarmellose Sodium, NF | 4.0 | 4.0 | 4.0 | 4.0 |
| Pregelatinized Starch, NF | 5.0 | 5.0 | 5.0 | 5.0 |
| Magnesium Carbonate, USP/NF | 1.0 | 2.0 | 2.0 | 2.0 |
| Talc, USP | 2.0 | 2.0 | 2.0 | 2.0 |
| Hydrogenated Vegetable Oil, Type I, USP/NF | 1.0 | 1.0 | 1.0 | 1.0 |
| Tablet weight (mg) | 125 | 150 | 400 | 800 |

Example 7

AD formulations Containing L-carnitine-L-tartrate

AD, 35–40% of the microcrystalline cellulose shown in the table, pregelatinized starch, one-half of the of croscarmellose sodium shown in the table, and magnesium carbonate were mixed, wet granulated using water (about 8%) in a high shear mixer (Niro-Fielder model PMA 25). After wet-milling, the granules were dried and dry-milled (Quadro Co-Mil model 197S) to appropriate particle size (200–500 μm). Then the granules were powder blended with the remaining 50% of croscarmellose sodium, and the remaining 60–65% of microcrystalline cellulose for 3–10 minutes. The powder blend was mixed with sodium stearyl fumarate for another 3–5 minutes.

The powder blend was compressed into tablets on an instrumental 16 station rotary tablet press (β-type, Manesty).

| Component | 5 mg % w/w | 10 mg % w/w | 30 mg % w/w | 60 mg % w/w | 30 mg % w/w |
|---|---|---|---|---|---|
| AD | 4.0 | 6.7 | 7.5 | 7.5 | 4.0 |
| L-Carnitine-L-Tartrate | 24.0 | 49.3 | 45.0 | 45.0 | 48.0 |
| Microcrystalline Cellulose, NF | 61.0 | 32.0 | 35.5 | 35.5 | 36.0 |
| Croscarmellose Sodium, NF | 4.0 | 4.0 | 4.0 | 4.0 | 4.0 |
| Pregelatinized Starch, NF | 5.0 | 5.0 | 5.0 | 5.0 | 5.0 |
| Magnesium Carbonate, USP | 1.0 | 2.0 | 2.0 | 2.0 | 2.0 |
| Sodium Stearyl Fumarate | 1.0 | 1.0 | 1.0 | 1.0 | 1.0 |
| Tablet weight (mg) | 125 | 150 | 400 | 800 | 750 |

Example 8

Stability of AD Formulation Containing L-carnitine-L-tartrate

Tablets consisting of three different formulations with 360 mg L-carnitine-L-tartrate per tablet and weighing 800 mg were prepared essentially as described in example 6. The tablets were set up on stability and AD was analyzed at designated time points shown below. The first formulation, lot #A, contained 60 mg AD and 16 mg magnesium carbonate hydroxide per tablet. The second formulation, lot #B, contained 60 mg AD and no alkaline excipient and additional microcrystalline cellulose to keep tablet weight at 800 mg. The third formulation, lot #C, contained 60 mg AD and 16 mg calcium carbonate. For the stability study, thirty tablets were packaged in an induction-sealed 75 mL HDPE bottle (Wheaton Drawing No. B-23487B) each with either one, three, or five grams of silica gel. AD remaining at different time points was determined by an area normalization method.

Results obtained from incubating lots #A–C at 60° C./75% RH (induction-sealed HDPE bottle) are shown below.

| Lot | SG(g) | % AD Remaining | | | | |
|---|---|---|---|---|---|---|
| | | 0 wk | 1 wk | 2 wk | 3 wk | 4 wk |
| #A | 1 | 99.6 | 96.7 | 94.8 | 88.5 | — |
| | 3 | 99.6 | 97.3 | 95.2 | 93.6 | — |
| | 5 | 99.6 | — | 96.9 | 94.6 | 92.0 |
| #B | 1 | 99.5 | 89.4 | 65.9 | 6.9 | — |
| | 3 | 99.5 | 92.8 | 85.9 | 64.1 | — |
| | 5 | 99.5 | — | 90.5 | 78.7 | 66.4 |
| #C | 1 | 99.6 | 97.0 | 97.8 | — | — |
| | 3 | 99.6 | 96.6 | 95.4 | — | — |
| | 5 | 99.6 | — | 95.2 | 92.8 | — |

Results obtained from incubating lots #A–C at 40° C./75% RH (induction-sealed HDPE bottle) are shown below.

|     |       | % AD Remaining |       |       |       |       |       |       |       |       |
| --- | ----- | -------------- | ----- | ----- | ----- | ----- | ----- | ----- | ----- | ----- |
| Lot | SG(g) | 0 mon          | 2 mon | 3 mon | 4 mon | 5 mon | 6 mon | 7 mon | 8 mon | 9 mon |
| #A  | 1     | 99.6           | —     | 97.6  | —     | 96.4  | 95.4  | 93.0  | —     | —     |
|     | 3     | 99.6           | —     | 97.8  | —     | —     | 96.9  | 96.0  | 95.7  | —     |
|     | 5     | 99.6           | —     | —     | —     | —     | 96.8  | 95.2  | 95.9  | 96.2  |
| #B  | 1     | 99.5           | —     | 93.2  | 89.7  | 84.6  | 71.3  | 38.6  | —     | —     |
|     | 3     | 99.5           | —     | 95.4  | —     | 93.9  | 92.6  | 90.0  | 88.0  | —     |
|     | 5     | 99.5           | —     | —     | —     | —     | 94.6  | 92.4  | 93.0  | 92.3  |
| #C  | 1     | 99.6           | —     | —     | —     | 94.8  | 93.6  | 91.9  | —     | —     |
|     | 3     | 99.6           | —     | —     | —     | —     | 95.6  | 94.3  | 93.7  | —     |
|     | 5     | 99.6           | —     | —     | —     | —     | 96.5  | 95.4  | 94.9  | 94.4  |

Example 9

AD Degradation Products

Studies have shown that AD decomposes as shown below. The decomposition products are useful to monitor and analyze compositions containing in AD formulations, e.g., they may be detected by HPLC or other analytical standards.

HYDROLYSIS

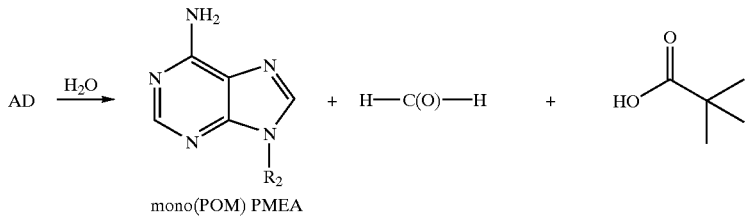

mono(POM) PMEA

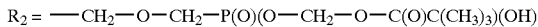

$R_2 = -CH_2-O-CH_2-P(O)(O-CH_2-O-C(O)C(CH_3)_3)(OH)$

DIMERIZATION

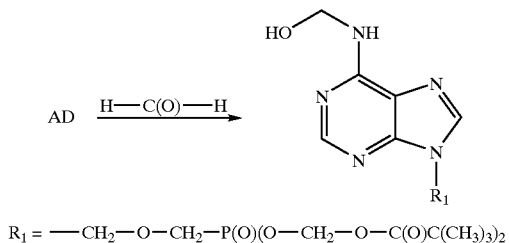

$R_1 = -CH_2-O-CH_2-P(O)(O-CH_2-O-C(O)C(CH_3)_3)_2$

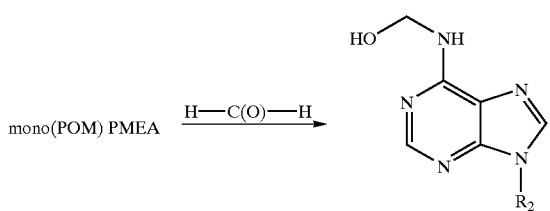

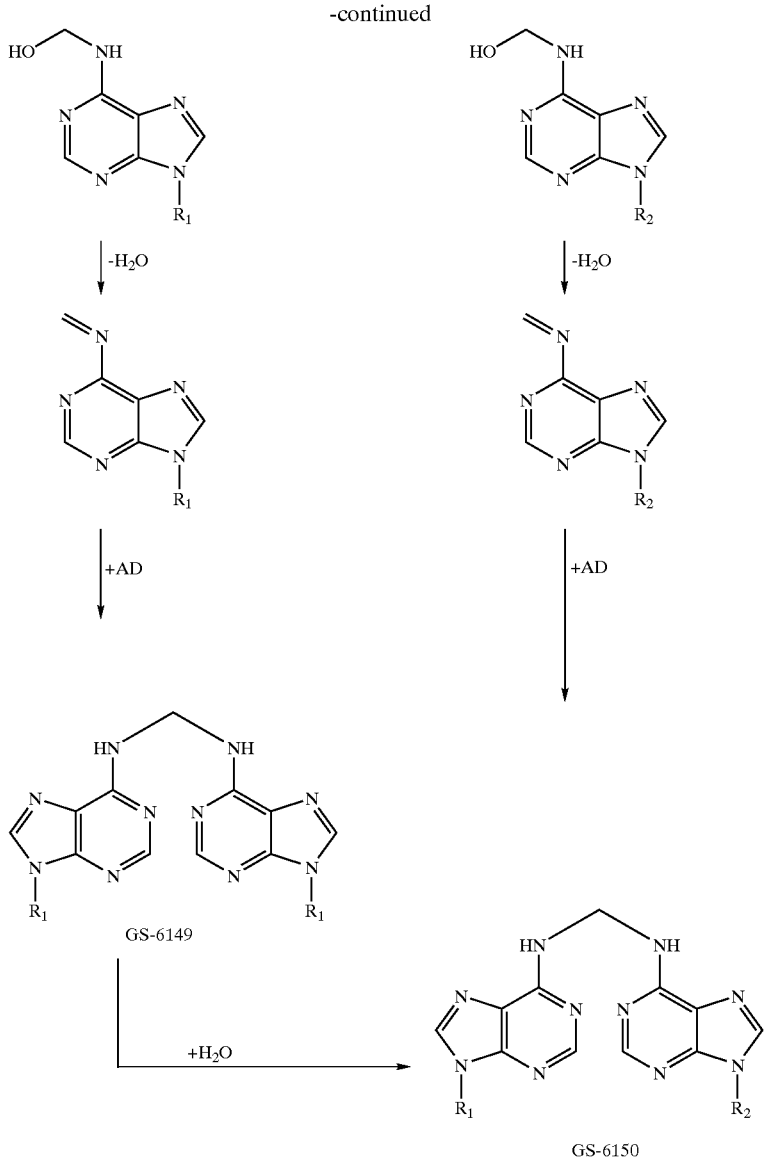

The table below summarizes the product distribution after storage at 60° C. and 30% RH for formulations containing AD, L-carnitine-L-tartrate and 2% MgCO$_3$ (lot #A), 2% CaCO$_3$ (lot #C) or a control formulation containing no alkaline excipient (lot #B). Example 8 above describes these formulations. Thirty tablets were packaged in an induction-sealed 75 mL HDFE bottle (Wheaton Drawing No. B-23487B) each with either one, three, or five grams of silica gel. Addition of these carbonates appeared to reduce the rate of cross-linking reaction, leading to the formation of lower levels of GS-6149 and GS-6150.

| Lot | SG (g) | Time[2] | AD[1] | mono-POM | GS-6147 | GS-6148 | GS-6149 | GS-6150 | others[3] |
|---|---|---|---|---|---|---|---|---|---|
| #A | 1 | 6 | 95.4 | 2.8 | 0 | 0.9 | 0.6 | 0.4 | 0 |
| #C | 5 | 6 | 94.6 | 2.8 | 0 | 1.0 | 0.9 | 0.7 | 0 |
| #B | 1 | 7 | 94.3 | 3.3 | 0 | 1.1 | 0.6 | 0.3 | 0.4 |
| #C | 5 | 7 | 92.4 | 3.3 | 0 | 1.5 | 1.2 | 1.2 | 0.4 |
| #B | 1 | 7 | 91.9 | 4.4 | 0 | 1.6 | 0.6 | 0.6 | 1.0 |
| #C | 3 | 7 | 90.0 | 4.2 | 0 | 1.9 | 1.7 | 1.6 | 0.5 |
| #B | 3 | 8 | 94.9 | 3.3 | 0 | 0 | 0.4 | 0.3 | 1.1 |
| #C | 5 | 8 | 93.0 | 3.5 | 0 | 0 | 1.1 | 0.9 | 1.5 |

[1]% AD remaining was determined using an area normalization method.
[2]Time in months.
[3]The total amount of other known degradation products.

Example 10

Preparation of Crystalline AD

Anhydrous crystalline AD was prepared essentially as described in U.S. application Ser. No. 08/900,745. An exemplary preparation was conducted as follows. 9.7 kg of N-methylpyrrolidone (NMP) at room temperature was added to 3 kg of PMEA in a 30 gallon glass-lined steel reactor vessel (Pfaudler, Rochester, N.Y., model No. P20-30-150-115) and the mixture was moderately agitated after NMP was added. The moderate agitation used was sufficient to maintain solid PMEA in suspension and a shallow vortex was present, but agitation was not vigorous and splashing of reactor contents did not occur. 5.6 kg of TEA was then added, followed by addition of 8.3 kg of chloromethyl pivalate. An additional 2.7 kg of NMP was then added to wash residual materials from the transfer lines used to feed the reactor. The temperature was adjusted to about 48° and the temperature was maintained between 38–48° for 18 hours with moderate agitation. After the reaction was complete, 48 kg of isopropyl acetate at room temperature was added to the reactor and the resulting mixture was maintained for 1 hour at 43–48° with moderate agitation, followed by filtration of the reaction mixture to remove the solids (Tyvek™ filter, 15.5" diameter, Kavon Filter Products, Wall, N.J., model No. 1058-D). The filtrate was transferred to a 50 gallon glass-lined steel reactor vessel (Pfaudler, model No. P24-50-150-105) while maintaining the temperature at 43–48° and the 30 gallon vessel was washed with 12 kg of isopropyl acetate at 43–48° to rinse the vessel. This wash was transferred to the 50 gallon reactor and the temperature was allowed to drop to ambient during subsequent steps.

The mixture was then washed with 22 kg of water by vigorous agitation (deep vortex with splashing of reactor contents) for about 1.5–2 minutes. Agitation was discontinued and the phases were allowed to completely separate (about 10 min). The lower aqueous phase (about 26 L) was transferred to the 30 gallon glass-lined steel reactor vessel. Another 22 kg of water was added to the organic phase left in the 50 gallon reactor and the phases were vigorously agitated for about 1.5–2 minutes. Agitation was discontinued and the phases were allowed to completely separate (about 1 hour 40 min). The lower aqueous phase was transferred to the 30 gallon glass-lined steel reactor vessel which now contained both aqueous washes. 24 kg of isopropyl acetate was added to the aqueous washes in the 30 gallon reactor and the phases were vigorously agitated for about 1.5–2 minutes, followed by discontinued agitation and phase separation for sufficient time to obtain complete phase separation (about 10 min). The upper organic phase was retained and mixed with the organic phase previously retained in the 50 gallon reactor. 24 kg of isopropyl acetate was added to the aqueous washes in the 30 gallon reactor and the phases were vigorously agitated for about 1.5–2 minutes, followed by discontinued agitation and phase separation for sufficient time to obtain complete phase separation (about 20 min). The upper organic phase was retained and mixed with the organic phase previously retained in the 50 gallon reactor. The combined organic phases were then washed with a brine solution (7 kg water, 3.9 kg NaCl) by vigorous agitation for about 1.5–2 minutes followed by discontinued agitation to allow the phases to completely separate (about 5 min). The brine wash was discarded. The combined organic phase was drained from the 50 gallon reactor and 18 kg of sodium sulfate was added to the reactor, followed by adding the organic phase back to the reactor and agitating vigorously for about 1.5–2 minutes to mix the reactor contents and then allowing the mixture to stand for 1 hour. The organic phase weighed 98.5 kg at this point.

The reactor contents were then gently agitated and the contents were transferred to a bag filter (American Felt and Filter Co, model No. RM C S/S 122) and filtered under low nitrogen pressure applied to the reactor. The organic phase containing AD was transferred to a clean 50 gallon reactor and volatile organics were removed by vacuum distillation for 2 hours 25 minutes until no volatile components were observed to condense in the distillation receiving container. The organic phase temperature was maintained at 33°–41° C. at a vacuum of 26–30" Hg until the organic phase volume had a volume of 50–55 L. The organic phase was transferred from the 50 gallon reactor to a clean 30 gallon reactor via vacuum filtration using a cartridge filter (Memtec America, Corp., model No. 910044) containing a cotton spun wound cartridge (a polypropylene spun wound cartridge can also be used). 8.6 kg of isopropyl acetate was added to the 50 gallon reactor and this was transferred from the 50 gallon reactor and added to the organic phase in the 30 gallon via vacuum filtration. The organic phase was held overnight at 5°. Vacuum distillation was continued in the 30 gallon reactor at 26°–41° for 3 hours to obtain about 7–9 L of oil containing AD. 5.4 kg of acetone was added to the oil which yielded a clear solution. The solution was then agitated and warmed to 43° C. and 27 kg of di-n-butyl ether at room temperature was added over a period of about 4 minutes followed by warming to return the temperature to 43° C. An additional 15 kg of di-n-butyl ether was added over about 4 minutes and the temperature was returned to 43°–44° C. at which time the temperature was allowed to drop to 20° C. over about 7 hours 15 minutes. During this time AD crystals formed in the reactor. The crystals were recovered by filtering (Nutche filter) at about 5 psi above atmospheric pressure under nitrogen. 2.40 kg of dried anhydrous AD crystal was recovered (45.1%).

We claim:

1. A composition consisting essentially of 9-[2-[bis(pivaloyloxy)methyl]phosphonomethoxyl]ethyl]adenine and an alkaline excipient, having a pKa of the conjugated acid of at least about 4.0 and a Ksp of about $1\times10^{-3}$ to about $1\times10^{-15}$.

2. The composition of claim 1 wherein the loss on drying (LOD) at 75° C. is no more than 5%.

3. The composition of claim 2 wherein the alkaline excipient is an alkaline carbonate or an alkaline hydroxide.

4. The composition of claim 3 wherein the alkaline carbonate is calcium carbonate, magnesium carbonate, zinc carbonate, manganese carbonate, aluminum carbonate, ferrous carbonate or cobalt carbonate.

5. The composition of claim 2 wherein the alkaline hydroxide is magnesium hydroxide, calcium hydroxide, aluminum hydroxide or iron hydroxide.

6. The composition of claim 2 wherein the LOD 75° C. is no more than about 2%.

7. The composition of claim 2 wherein the LOD 75° C. is no more than about 1.5%.

8. The composition of claim 1 wherein the alkaline excipient comprises about 1–20% of the composition.

9. The composition of claim 8 wherein the alkaline excipient is an alkaline carbonate or an alkaline hydroxide.

10. The composition of claim 9 wherein the alkaline carbonate is calcium carbonate, magnesium carbonate, zinc carbonate, manganese carbonate, aluminum carbonate, ferrous carbonate or cobalt carbonate.

11. The composition of claim 9 wherein the alkaline hydroxide is magnesium hydroxide, aluminum hydroxide or iron hydroxide.

12. The composition of claim 9 wherein the alkaline excipient comprises about 2–6%.

13. The composition of claim 8 wherein the composition is a unit dose.

14. The unit dose of claim 13 comprising a tablet containing about 1.0–300 mg of 9-[2-[[bis[(pivaloyloxy)methyl]phosphono]methoxy]ethyl]adenine.

15. The tablet or capsule of claim 13 wherein the tablet or capsule comprises about 5–30% w/w of 9-[2-[[bis[(pivaloyloxy)methyl]phosphono]methoxy]ethyl]adenine.

16. The tablet or capsule of claim 15 wherein the tablet or capsule comprises about 2–6% w/w of an alkaline excipient.

17. The tablet of claim 16 wherein the tablet comprises about 2–6% w/w of an alkaline excipient selected from the group consisting of calcium carbonate, magnesium carbonate, zinc carbonate, manganese carbonate, aluminum carbonate, ferrous carbonate and cobalt carbonate.

18. The tablet of claim 17 wherein the tablet comprises about 35–80% w/w of lactose monohydrate, anhydrous lactose, or microcrystalline cellulose.

19. The tablet or capsule of claim 17, wherein the tablet or capsule comprises about 20–50% w/w L-carnitine-L-tartrate, L-carnitine-L-fumarate or microencapsulated L-carnitine, about 4–20% w/w 9-[2-[[bis[(pivaloyloxy)methyl]phosphono]methoxy]ethyl]adenine and about 1–6% w/w alkaline excipient.

20. The composition comprising about 10 mg of 9-[2-[[bis[(pivaloyloxy)-methyl]phosphono]methoxyl]ethyl]adenine, about 1–5 mg magnesium carbonate or calcium carbonate, about 4–8 mg croscarmellose sodium, about 5 mg pregelatinized starch, about 40–65 mg lactose, about 15–35 mg microcrystalline cellulose, about 0–6 mg talc, and about 0.5–2 mg magnesium stearate.

21. The composition comprising about 30 mg of 9-[2-[[bis[(pivaloyloxy)-methyl]phosphono]methoxyl]ethyl]adenine, about 410 mg magnesium carbonate, 61.5–75.25 mg lactose monohydrate or anhydrous lactose, about 22.5 mg of microcrystalline cellulose, about 7.5 mg of pregelatinized starch, about 9 mg of croscarmellose sodium, about 0–9 mg talc and about 0.75–1.5 mg magnesium stearate.

22. The composition comprising about 60 mg of 9-[2-[[bis[(pivaloyloxy)-methyl]phosphono]methoxyl]ethyl]adenine, about 12 mg magnesium carbonate, about 73 mg lactose monohydrate or anhydrous lactose, about 30 mg of microcrystalline cellulose, about 10 mg of pregelatinied starch, about 12 mg of croscanellose sodium, about 1 mg silicon dioxide and about 2 mg magnesium stearate.

23. The composition comprising about 120 mg of 9-[2-[[bis[(pivaloyloxy)-methyl]phosphono]methoxyl]ethyl]adenine, about 12–24 mg magnesium carbonate, about 124–162 mg lactose monohydrate or anhydrous lactose, about 60 mg microcrystalline cellulose, about 20 mg pregelatinized starch, about 24 mg of croscarmellose sodium, about 0–24 mg talc and about 2–4 mg magnesium stearate.

24. The composition comprising about 4–8% w/w of 9-[2-[[bis[(pivaloyloxy)-methyl]phosphono]methoxyl]ethyl]adenine, about 16–% w/w magnesium carbonate, about 24–51% w/w L-carnitine-L-tartrate, about 20–36% w/w niicrocrystalline cellulose, about 5% w/w pregelatinized starch, about 4% w/w croscarmellose sodium and (1) about 1% w/w sodium stearyl fumarate or (2) about 2% w/w talc and about 1% w/w type I hydrogenated vegetable oil.

25. The composition of claim 1 in the form of dried granules having a LOD of no more than about 2.0%.

26. The composition of claim 1 which contains an additional excipient selected from the group consisting of a binder, disintegrant, diluent, lubricant, glidant, coloring agent and flavoring agent.

* * * * *